United States Patent
Qin et al.

(10) Patent No.: US 11,725,006 B2
(45) Date of Patent: Aug. 15, 2023

(54) HYDROPHILIC BERBERINE-TYPE DERIVATIVE AND APPLICATION THEREOF IN PREPARING DRUG

(71) Applicant: INSTITUTE OF MATERIA MEDICA, CHINESE ACADEMY OF MEDICAL SCIENCES, Beijing (CN)

(72) Inventors: Hailin Qin, Beijing (CN); Lianqiu Wu, Beijing (CN); Xiang Li, Beijing (CN); Haijing Zhang, Beijing (CN); Li Song, Beijing (CN); Huachen Song, Beijing (CN); Anjun Deng, Beijing (CN); Xiaonan Tang, Beijing (CN); Zhihui Zhang, Beijing (CN); Xiang Li, Beijing (CN); Zhihong Li, Beijing (CN)

(73) Assignee: INSTITUTE OF MATERIA MEDIC, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 17/046,927

(22) PCT Filed: Oct. 17, 2019

(86) PCT No.: PCT/CN2019/082701
§ 371 (c)(1),
(2) Date: Oct. 12, 2020

(87) PCT Pub. No.: WO2019/196957
PCT Pub. Date: Oct. 17, 2019

(65) Prior Publication Data
US 2021/0147409 A1    May 20, 2021

(30) Foreign Application Priority Data

| Apr. 13, 2018 | (CN) | 201810328506.3 |
| Apr. 13, 2018 | (CN) | 201810328605.1 |
| Apr. 13, 2018 | (CN) | 201810328741.0 |
| Apr. 13, 2018 | (CN) | 201810328743.X |
| Apr. 13, 2018 | (CN) | 201810328797.6 |

(51) Int. Cl.
| C07D 455/03 | (2006.01) |
| A61P 31/04 | (2006.01) |
| A61P 29/00 | (2006.01) |
| A61P 1/04 | (2006.01) |
| A61P 31/10 | (2006.01) |
| A61P 35/00 | (2006.01) |
| C07D 493/14 | (2006.01) |
| C07D 493/22 | (2006.01) |

(52) U.S. Cl.
CPC .............. *C07D 455/03* (2013.01); *A61P 1/04* (2018.01); *A61P 29/00* (2018.01); *A61P 31/04* (2018.01); *A61P 31/10* (2018.01); *A61P 35/00* (2018.01); *C07D 493/14* (2013.01); *C07D 493/22* (2013.01)

(58) Field of Classification Search
CPC ................................................... C07D 455/03
See application file for complete search history.

(56) References Cited

U.S. PATENT DOCUMENTS

2010/0113494 A1* 5/2010 Hu ............................ A61P 3/06
514/279

FOREIGN PATENT DOCUMENTS

| CN | 1923199 A | 3/2007 |
| CN | 101787029 A | 7/2010 |
| WO | 2004/093876 A2 | 11/2004 |

OTHER PUBLICATIONS

McMahon et al (2000).*
Pinedo et al. (2000).*
International Search Report for International Patent Application No. PCT/CN2019/082701 dated Jul. 19, 2019, 3 pages.
Iwasa, K. et al., "Antimicrobial Activity of 8-Alkyl- and 8-Phenyl-Substituted Berberines and Their 12-Bromo Derivatives", J. Nat. Prod., 61: 1150-1153 (1998).
Jiang, X., "Study on the Synthesis of 8-Alkyl-Coptisine Homologues and Their Pharmacological Activities", Chinese Doctoral Dissertations Full-text Database, Medical and Health Sciences, 93 pages (2011) (English Abstract).

(Continued)

*Primary Examiner* — Paul V Ward
(74) *Attorney, Agent, or Firm* — Merchant & Gould P.C.

(57) ABSTRACT

An 8-dihalomethyl berberine-type quaternary ammonium salt compound represented by general formula (I) or (II) and an application thereof in preparing a drug. The compound shows hydrophilicity and has antimicrobial, anti-inflammatory, anti-ulcerative colitis, and antitumor activities, while having no or low toxicity.

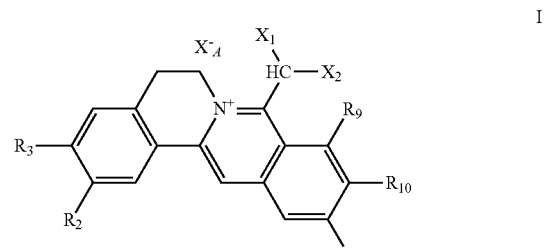

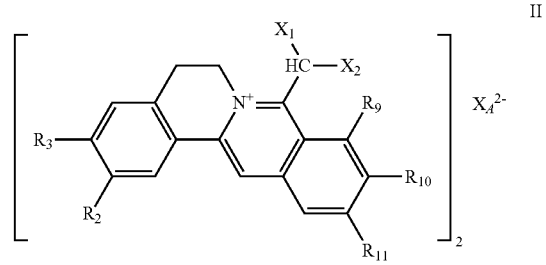

11 Claims, 3 Drawing Sheets

(56) References Cited

OTHER PUBLICATIONS

Li, B. et al., "Advances in the Study of Berberine and its Derivatives", Acta Pharmaceutica Sinica, 43(8): 773-787 (2008) (English Abstract).

Yang, Y., "Study on the Synthesis of 8-Alkyl-Berberine Homologues and Their Pharmacological Activity", Chinese Doctoral Dissertations Full-text Database, Medical and Health Sciences, 129 pages (2008) (English Abstract).

* cited by examiner

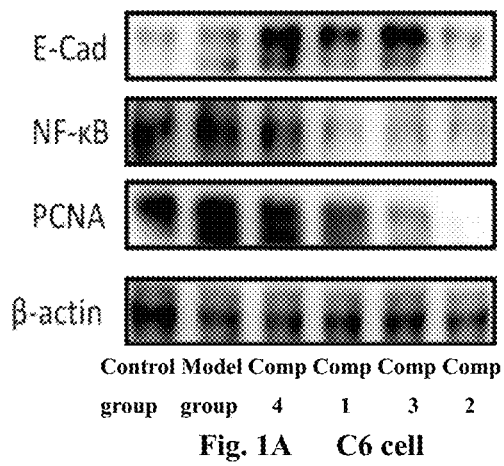
Fig. 1A    C6 cell
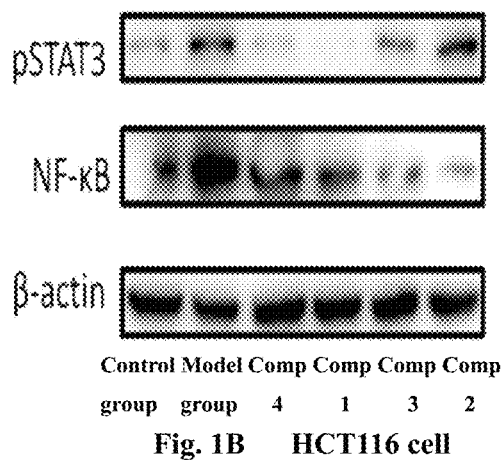
Fig. 1B    HCT116 cell
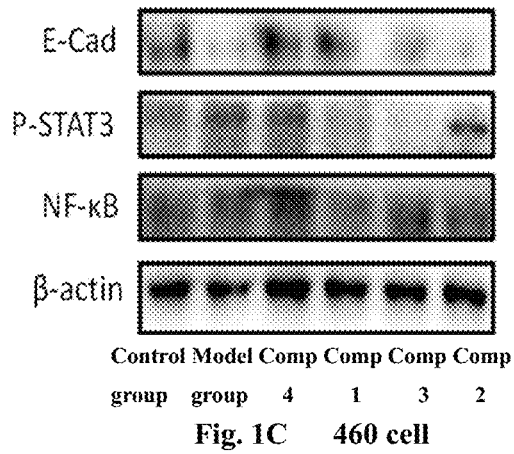
Fig. 1C    460 cell

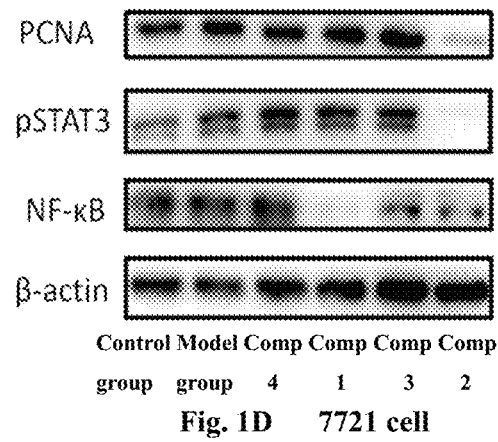
Fig. 1D  7721 cell
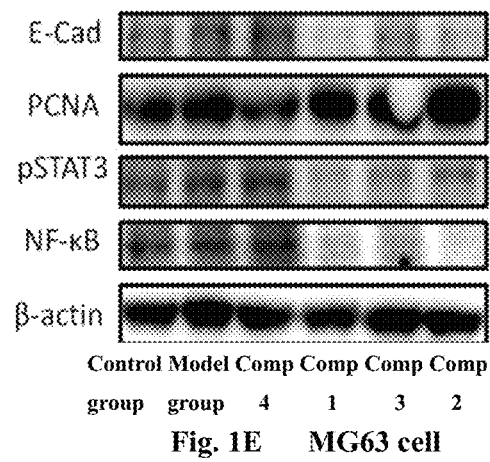
Fig. 1E  MG63 cell
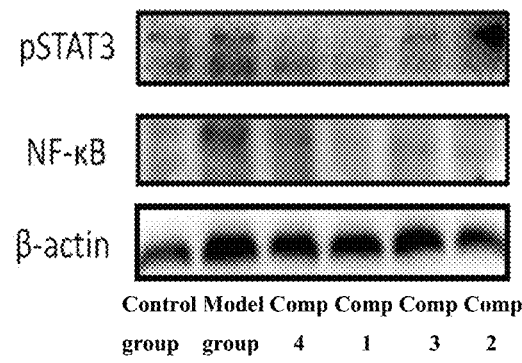
Fig. 1F  MDA-MB-231 cell

HYDROPHILIC BERBERINE-TYPE DERIVATIVE AND APPLICATION THEREOF IN PREPARING DRUG

This application is a National Stage Application of PCT/CN2019/082701, filed 15 Apr. 2019, which claims benefit of priority to Serial Nos. 201810328506.3, 201810328743.X, 201810328605.1, 201810328741.0, 201810328797.6 filed 13 Apr. 2018 in China, and which applications are incorporated herein by reference. To the extent appropriate, a claim of priority is made to each of the above disclosed applications.

TECHNICAL FIELD

This invention relates to hydrophilic 8-dihalomethyl berberine-type quaternary ammonium salt compounds of quaternized imine-type structure with hypotoxicity or nontoxicity which are synthesized using natural berberine-type alkaloid quaternary ammonium salts substrate as raw materials, the preparation method of the compounds in the invention, and the pharmacological activities of the compounds in the invention against cancers, microbial infections, inflammations, and ulcerative colitis. The compounds of the invention have obvious hydrophilicity compared with the natural alkaloids of berberine-type quaternary ammonium salt substrates. Pharmacological activity screening experiments conducted with the compounds of the invention demonstrated that the 8-dihalomethyl berberine-type quaternary ammonium salt compounds of quaternized imine-type structure of the invention have significant activities of anticancers, anti-microbial infections, anti-inflammations, and anti-ulcerative colitis. The characteristics of non-toxicity or hypotoxicity of the compounds of the invention were also demonstrated. The compounds of the invention can be used to prepare drugs to prevent, alleviate and/or treat cancers, microbial infections, inflammations, and ulcerative colitis. And the obvious hydrophilicity of the compounds of the invention facilitates the administration mode which is of great practical value to search for new pharmacological activities and improve the action intensity of drugs. The present invention belongs to the technical field of medicine.

BACKGROUND ART

Natural berebrine-type alkaloids are mainly 1-benzyltetrahydroisoquinoline compounds (or directly called as benzylisoquinoline compounds), which refer to the following three different types of compounds in the field of natural organic chemistry: (1) berberine-type quaternary ammonium compounds with the basic structure of 5,6-dihydroisoquinolino[3,2-a] isoquinolin-7-ium (I), (2) dihydroberberine-type compounds with the basic parent structure of 6,8-dihydro-5H-isoquinolino[3,2-a] isoquinoline (II), and (3) tetrahydroberberine-type compounds with the basic parent structure of 6,8,13,13a-tetrahydro-5H-isoquinolino[3,2-a] isoquinoline and their salts (III). The parent structures of the three subclasses are shown in chemical formulae 1. According to the structural analysis, the berberine-type quaternary ammonium salt compounds (I) and the dihydroberberine-type compounds (II) have multiple different resonance formulae shown in formulae 2 and 3, respectively. However, because of their different structures, their resonant structures and numbers may not be the same. There are also significant differences of structural characteristics between the structures of these two subclasses of compounds and those of tetrahydroberberine-type compounds of the basic carbon skeleton structure of 6,8,13,13a-tetrahydro-5H-isoquinolino [3,2-a]isoquinoline and their salts (III), that is, in III, besides the position 13a asymmetric center, there are only two individual benzene rings left in the product due to the reduction of the double bond between C-13 and C-13a to single bond (no more conjugation), the nitrogen atom being a localized structure. Or III can be considered as diphenylethane derivatives, and thus, is more significantly different from I and II. Of course, as for I and II, the former being quaternary ammonium salt-type compounds, the latter free tertiary amine-type compounds, and obvious differences in the conjugation situation between them existing, there are differences or significant differences involved in the physical and chemical properties, and others, such as solubility, chemical reactivity, and biological activity, of the two classes of compounds. Thus, from the perspective of organic chemistry, pharmaceutical chemistry, and pharmacy, berberine-type quaternary ammonium salt compounds and dihydroberberine-type compounds belong to different structural types.

Formulae 1. Basic structures of berberine-type quaternary ammonium salts (I), dihydroberberine-type compounds (II), and tetrahydroberberine-type compounds (III).

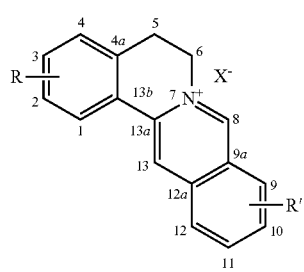

I

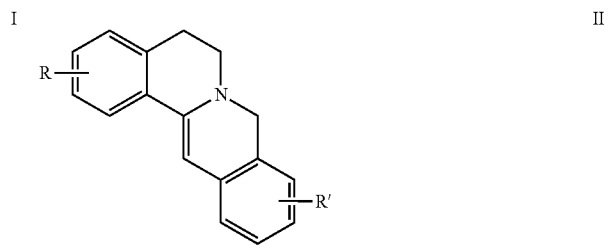

II

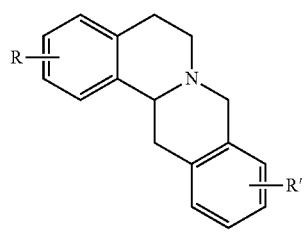

III

-continued

Formulae 2. Resonance formulae of berberine-type quaternary ammonium salt compounds (I).

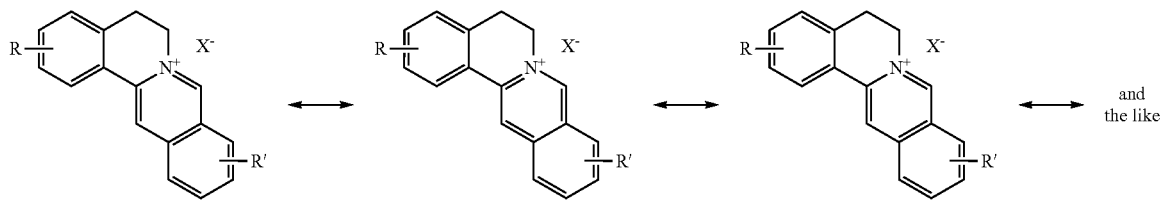

I

Formulae 3. Resonance formulae of dihydroberberine-type compounds (II).

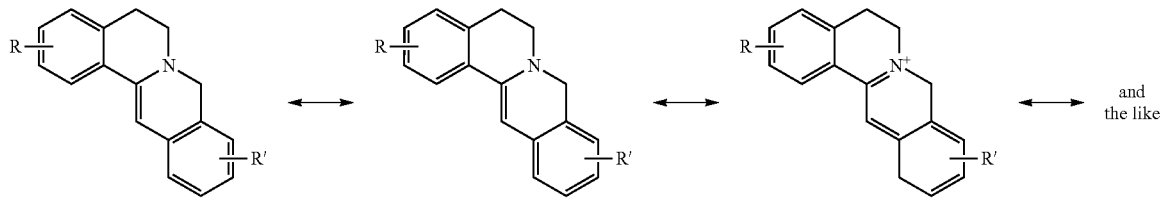

II

The common quaternary ammonium salts of natural berberine-type alkaloids include the quaternary ammonium salts of berberine, palmatine, coptisine, epiberberine, jatrorrhizine, and pseudocoptisine, etc. The corresponding tetrahydro-type reduction products of these natural products of imine-type quaternary ammonium are also abundant in nature. The quaternary ammonium salts of these berberine-type alkaloids can also be obtained by organic syntheses. In addition, other quaternary ammonium salts of berberine-type alkaloids can also be obtained by organic syntheses. Natural quaternary ammonium salts of berberine-type alkaloids and tetrahydroberberine-type compounds widely exist in many natural plants, for example, in plants of Ranunculaceae, Berberidaceae, and Papaveraceae families, etc. The existence of natural dihydroberberine-type compounds is relatively rare. Many kinds of berberine-type alkaloids have pharmacological effects, for example, coptisine quaternary ammonium salt has inhibition activity of A-type monoamine oxidase, selective inhibition activity of vascular smooth muscle cell (VSMC) proliferation, inhibition activity of osteoclast differentiation and function, double inhibition activity of VSMC proliferation, selective regulation activity of multidrug resistance proteins in VSMC, antifungal activity, myocardial protective activity, and gastric mucous membrane protection activity, etc [Zhi-Hui Zhang et al., China Journal of Chinese Materia Medica, 2013, 38(17):2750]. Berberine quaternary ammonium salt has activities of anti-pathogenic microbes, anti-inflammation, anti-tumor, heart protection, hypoglycaemia, regulation of lipid metabolism, and immunosuppression, etc [Yu Xing, et al., Chinese Journal of Pharmacology and Toxicology, 2017, 31(6):491]; palmatine quaternary ammonium salt has antibacterial activity, etc [Zhi-Cheng Li, et al., Guangdong Chemical Industry, 2015, 42(8):7]. At present, some compounds of quaternary ammonium salts of berberine-type alkaloids or their reduction products have been used in clinical treatment of related diseases as listed drugs, for example, quaternary ammonium salts of berberine chloride (also known as berberine hydrochloride) is embodied in the Chinese Pharmacopoeia as an antibacterial agent. Berberine quaternary ammonium salt, palmatine quaternary ammonium salt, coptisine quaternary ammonium salt, epiberberine quaternary ammonium salt, and jatrorrhizine quaternary ammonium salt collectively are the main ingredients of Huangliansu, which is used in clinic to treat diarrhea caused by intestinal bacterial infection. L-tetrahydropalmatine as an analgesic was embodied in Chinese Pharmacopoeia, etc. However, considering the chemical structure and the relevant physical and chemical properties that have been established, the quaternary ammonium salts of berberine-type alkaloids have poor solubility in pure water and common organic solvents, which leads to poor bioavailability and poor pharmacological effects and is adverse to druggability. Of course, the property of poor solubility can also be applied for some special medical needs, for example, the above-mentioned application of berberine-type quaternary ammonium salt alkaloid in the clinical treatment of intestinal infection diseases is precisely to use this poor solubility, which can achieve direct effect on intestinal lesions without absorption. However, there is no doubt that in most cases, the improvement of solubility is beneficial to enhancing the pharmacological action of drugs on organisms. In other words, solubility has an impact on the drug effect, but the specific situation needs to be analyzed. In the disclosed research data, the antibacterial activity of 13-substituted and 9-modified quaternary ammonium salt of berberine-type alkaloids showed a certain degree of improvement compared with the substrate. However, the reduction of the substrate to tetrahydroberberine-type compounds lead to the decrease of antibacterial activity. Thus, it is concluded that the quaternary ammonium structure, spatial effect, and the improvement of lipophilicity of substituents can improve the antibacterial activity of the substrates. Although the N-methyl-type quaternary ammonium salt structure of tetrahydroberberine-type compounds can improve the antibacterial activity compared with the tertiary amine structure, this effect is relatively weak. And the investigated compounds showed strong antibacterial activity against *Staphylococcus aureus* (Gram-positive bacteria) and weak antibacterial effect on *Escherichia coli* (Gram-negative bacteria) and *Candida albicans* (fungi) (Iwasa K, et al. Eur J Med Chem, 1996, 31:469; Iwasa K, et al. Planta Med, 1997, 63:196; Iwasa K, et al. Planta Med, 1998, 64:748). The introduction of alkyl or phenyl at C-8 and/or bromine at C-12 can also increase the antibacterial activity to some extent. And in the case of less than eight carbon atoms, with the elongation of fatty chain (i.e. the increase of liposolubility), the antibacterial activity also increased (Iwasa K, et al. J Nat Prod, 1998, 61:1150; Ma T W, et. al. Letters in Drug Design & Discovery, 2011, 8: 464; Yang Y, et al. Planta Med, 2007, 73: 602). In the fields of anti-inflammatory and anti-tumor pharmaceutical chemistry of quaternary ammonium salt of natural berberine-type alkaloids, the disclosed research data are similar to those of antibacterial pharmaceutical chemistry in chemical research. The target structures were designed mainly based on the idea of investigating the structural modifications and transformations at 8-, 12-, and 13-positions of the substrates and the derivatives with different reduction degree of substrate (Zhang Z H, et al. Eur J Med Chem, 2014, 86,: 542; Zhang Z H, et al, J Med Chem, 2015, 58:7557; Xie M, et al. J Nat Prod, 2016, 79:775), and all the results were also the improvement of liposolubility. Pharmacological evaluation data showed that quaternary ammonium derivatives obtained by introducing alkyl at 8- and 13-positions of the substrates or introducing benzyls at 13-position and N, N-dibenzylamino at 8-position of the substrates all make for improving the cytotoxicity against human tumor cells. The 8-imino-dihydroberberine-type derivatives, 8-N-alkylimino-dihydroberberine-type derivatives, 12-aminoberberine-type quaternary ammonium derivatives, and 12-N,N-dialkylamine quaternary ammonium derivatives of the substrates also have effects on improving the cytotoxicity against human tumor cells. All kinds of skeleton-unsubstituted dihydroberberine-type derivatives and 8-acetonyl-substituted dihydroberberine-type derivatives have categorical and significant anti-ulcerative colitis activity, but they have the properties of unstable chemical structure, and are prone to structural changes in a variety of solvents, thus affecting the pharmacological effect. And the 8-imino-dihydroberberine-type derivatives which were designed and synthesized to improve the chemical stability of dihydroberberine-type derivatives showed no anti-ulcerative colitis activity. Only N-dihydrocoptisine-8-ylidene aromatic amine derivertives and N-dihydrocoptisine-8-ylidene aliphatic amide derivertives showed certain anti-ulcerative colitis activity (Xie M, et al. J Nat Prod, 2016, 79:775). Quaternary ammonium derivatives of 13-benzyl-substituted berberine-type also have certain anti-ulcerative colitis activity. All of these structure modifications improved the liposolubility of the substrates. Of these berberine-type quaternary ammonium derivatives with cytotoxicity against tumor cell lines, compounds bearing aliphatic hydrocarbon group at positions 8, 12, and 13 are usually hypertoxic to normal biological cells. Among the above active compounds against ulcerative colitis, dihydroberberine-type derivatives with the strongest activity and 8-acetonyl-substituted dihydroberberine-type derivatives have extremely unstable chemical properties.

Considering from the viewpoint of solubility, these disclosed research data are all to improve the liposolubility of quaternary ammonium salt precursors of natural berberine-type alkaloids. And the established structure-activity relationship was generally related to the improvement for liposolubility. For example, according to the disclosed information, by improving the liposolubility of quaternary ammonium salt of berberine-type derivatives, the absorption of the compounds in the body can be improved, so as to improve the bioavailability and enhance the pharmacological effect. Only by replacing different anions of quaternary ammonium salt substrates of berberine-type, such as replacing chloride ion with oxalate ion and other organic acid ions, the solubility or pharmacological effect did not significantly improve (Zhang Z H, et al. J Asian Nat Prod Res, 2016, 18(6):576). Due to the influence of the presence of organic nitrogen cation, the structure of quaternary ammonium salt substrates of berberine-type belongs to the passivation reaction structure in organic aromatic electrophilic substitution reaction. Therefore, the attempt to introduce hydrophilic functional groups, including carboxyl and sulfonic acid groups, into quaternary ammonium salt substrates of berberine-type has not been successful. The process for obtaining the compounds of the present invention has its particularity, the compounds of the invention being obtained by accident and at random. The preparation includes three synthetic steps: (1) The reaction materials, trihalomethyl anion, obtained under alkaline condition, was used as nucleophilic reagent to nucleophilic addition of substrates to obtain 8-trihalomethyl-dihydroberberine-type compounds; (2) The key intermediate 8-dihalomethylene-dihydroberberine-type derivatives were obtained by the elimination reaction of 8-trihalomethyl-dihydroberberine-type compounds under alkaline condition; (3) The compounds of the invention, 8-dihalomethyl berberine-type quaternary ammonium salt compounds of quaternized imine-type structure, were obtained by quaternization reaction of 8-dihalomethylene-dihydroberberine-type compounds in the presence of various acid species (The reaction result of Step 3 is unexpected). Wherein, in the last step of obtaining the compounds of the invention, due to the use of acid reagents, it is usually necessary to remove the residual acid from the product by washing it with water until the product is neutral. In this step, the hydrosolubility of the products was found, unexpectedly. And further, through extensive pharmacological activity screening, the recognition was learned that the compounds obtained by the invention showed a stronger pharmacological activity than the active substances obtained by the prior arts through the significant improvement of their hydrosolubility. Meanwhile, the toxicology experiment showed that the compounds of the invention also have the characteristics of non-toxicity or hypotoxicity. Pharmacodynamic experiments showed significant biological activity. The obvious hydrophilicity of the compounds of the invention facilitates the administration mode, which is of great practical value for searching for new pharmacological activities and improving the intensity of drug action and can be used to prepare drugs to prevent, alleviate, and/or treat multiple diseases.

The structures of the compounds of the invention have been identified by the spectroscopic methods. The solubility test experiment proved that the compounds of the invention have obvious hydrophilic improvement compared with the substrates, in addition to significant improvement of the solubility in polar organic solvent. The pharmacological activities evaluations combined with the target molecule experiment related to tumorigenesis proved that the compounds of the invention have antibacterial, anti-inflammatory, anti-ulcerative colitis, and anti-tumor activities, and have significant effects compared with the positive drug. The results of cytotoxic evaluation and animal acute toxicity evaluation showed that the compounds of the invention have no obvious toxicity to experimental cells of normal cell lines and experimental animals, and belong to hypotoxic or non-toxic compounds. Compared with parents of the quaternary ammonium of berberine-type alkaloids and the disclosed structural analogues, the hydrosolubility and biological activities of the compounds of the invention have been greatly improved, which is helpful to fundamentally overcoming the defects of inconvenient administration, poor bioavailability, and weak pharmacological action of the protoberberine-type alkaloids. Therefore, the compounds of the invention have significant application values in the preparation of anti-microbial infection, anti-inflammatory, anti-ulcerative colitis, and anti-tumor drugs.

To sum up, the poor solubility is one of the main obstacles in clinical application of the berberine-type quaternary ammonium salt compounds of imine-type structure. The improvement of liposolubility is helpful to improving the pharmacological effect, but it does not significantly improve the druggability due to the problems of toxicity, the intensity of pharmacological action, and the chemical structure stability, and so on. The compounds of the invention improved the hydrosolubility of the berberine-type quaternary ammonium salt compounds of imine-type structure, the solubility in the polar organic solvent, the intensity of the pharmacological action, the safety of clinical application, and the stability of the chemical structure. Therefore, it is of great significance for the discovery, research, and preparation of related drugs.

INVENTION CONTENTS

In extensive experiments, the inventor found that, by introducing unconventional dihalomethyl at the C-8 position of quaternary ammonium salt compound substrates of natural berberine-type alkaloid as a rare functional group to change the properties of organic compounds, the hydrophilicity of quaternary ammonium salt compounds of natural berberine-type alkaloid can also be improved. Based on these findings, the technical problem to be solved by the invention is to provide, by chemical syntheses, a class of hydrophilic berberine-type alkaloid derivatives and a preparation method thereof, and to provide pharmaceutical compositions with the compounds of the invention as the bioactive compounds and their applications in the preparation of antibacterial, anti-inflammatory, anti-ulcerative colitis, and anti-tumor drugs. The berberine-type quaternary ammonium salt compounds with novel structures and hydrophilic characteristics are synthesized in the present invention using a variety of quaternary ammonium salt of natural berberine-type alkaloids as raw materials, including berberine chloride quaternary ammonium salt and coptisine chloride quaternary ammonium salt. The improvement of hydrophilicity can provide apparent convenience for pharmacological experiments of intragastric administration using water as solvent and follow-up clinical application, and therefore, the intensity of pharmacological action of the compounds can be enhanced. Thus, in the case of obtaining compounds with hypotoxicity or even nontoxicity, the present invention significantly improves the druggability, and further facilitates the drug administration mode in pharmacological experiments and clinical medications. The present invention has remarkable application value in the preparation of antibacterial, anti-inflammatory, anti-ulcerative colitis, and antitumor drugs.

The technical problem solved by the present invention is to provide a class of berberine-type quaternary ammonium salt compounds with both novel structures and hydrophilic characteristics by means of chemical synthesis, i.e., 8-dihalomethyl berberine-type quaternary ammonium salt compounds of quaternized imine-type structure shown in general formulae I and II.

To solve the above technical problems, the present invention provides the following technical scheme:

The first aspect of the present invention provides hypotoxic and hydrophilic 8-dihalomethyl berberine-type quaternary ammonium salt compounds of quaternized imine-type structure as shown in general formulae I and II as the compounds of the invention.

The second aspect of the present invention provides the preparation methods of hypotoxic and hydrophilic 8-dihalomethyl berberine-type quaternary ammonium salt compounds of quaternized imine-type structure as shown in general formulae I and II.

The third aspect of the present invention provides pharmaceutical compositions of hypotoxic and hydrophilic 8-dihalomethyl berberine-type quaternary ammonium salt compounds of quaternized imine-type structure as shown in general formulae I and II.

The forth aspect of the present invention provides a use of hypotoxic and hydrophilic 8-dihalomethyl berberine-type quaternary ammonium salt compounds of quaternized imine-type structure as shown in general formulae I and II to prevent, alleviate and/or treat microbial infections.

The fifth aspect of the present invention provides a use of hypotoxic and hydrophilic 8-dihalomethyl berberine-type quaternary ammonium salt compounds of quaternized imine-type structure as shown in general formulae I and II to prevent, alleviate and/or treat inflammations.

The sixth aspect of the present invention provides a use of hypotoxic and hydrophilic 8-dihalomethyl berberine-type quaternary ammonium salt compounds of quaternized imine-type structure as shown in general formulae I and II to prevent, alleviate and/or treat ulcerative colitis.

The seventh aspect of the present invention provides utility of hypotoxic and hydrophilic 8-dihalomethyl berberine-type quaternary ammonium salt compounds of quaternized imine-type structure as shown in general formulae I and II to prevent, alleviate and/or treat tumors.

The chemical structure formulae of the 8-dihalomethyl berberine-type quaternary ammonium salt compounds of quaternized imine-type structure with the natures of hypotoxicity and hydrophilicity provided in the first aspect of the present invention as shown in general formulae I and II are shown in the following formulae I and II.

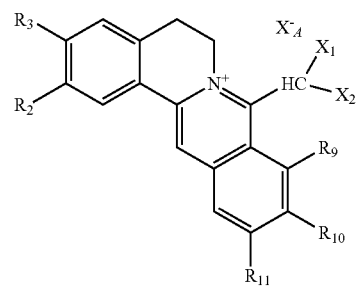

I $R_2$ and $R_3$ are selected, independently, from H, OH, or C1-C4 alkoxy, or $R_2$ and $R_3$ are linked to form alkylene-dioxy;

$X_1$ and $X_2$ are each selected, independently, from F (fluorine), Cl (chlorine), Br (bromine), or I (iodine);

$R_9$, $R_{10}$, and $R_{11}$ are selected, independently, from H, OH, or C1-C4 alkoxy, or $R_9$ and $R_{10}$ are linked to form alkylene-dioxy and $R_{11}$ is selected from H, or $R_9$ is selected from H and $R_{10}$ and $R_{11}$ are linked to form alkylene-dioxy;

$X_A^-$ is monovalent acid radical ion.

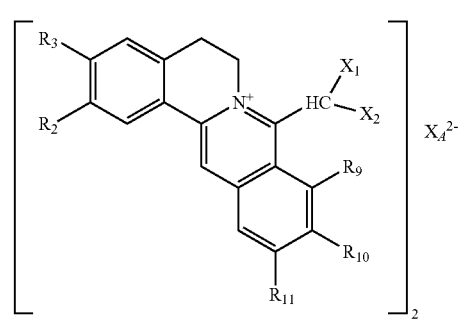

II $R_2$ and $R_3$ are selected from H, OH, or C1-C4 alkoxy, independently, or $R_2$ and $R_3$ are linked to form alkylene-dioxy;

$X_1$ and $X_2$ are each selected from F (fluorine), Cl (chlorine), Br (bromine), or I (iodine), independently;

$R_9$, $R_{10}$, and $R_{11}$ are selected from H, OH, or C1-C4 alkoxy, independently, or $R_9$ and $R_{10}$ are linked to form alkylene-dioxy and $R_{11}$ is selected from H, or $R_9$ is selected from H and $R_{10}$ and $R_{11}$ are linked to form alkylene-dioxy;

$X_A^{2-}$ is divalent acid radical ion.

Further, the chemical structure formulae of the 8-dihalomethyl berberine-type quaternary ammonium salt compounds of quaternized imine-type structure provided in the first aspect of the present invention with the natures of hypotoxicity and hydrophilicity are shown in the following formulae I and II:

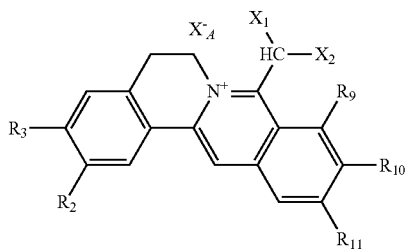

I when $R_2$ and $R_3$ are linked to form alkylene-dioxy, $R_9$ and $R_{10}$ are linked to form alkylene-dioxy and $R_{11}$ is selected from H;

or when $R_2$ and $R_3$ are linked to form alkylene-dioxy, $R_9$, $R_{10}$, and $R_{11}$ are selected from H, OH, or C1-C4 alkoxy, independently;

or when $R_2$ and $R_3$ are selected from H, OH, or C1-C4 alkoxy, independently, $R_9$ and $R_{10}$ are linked to form alkylene-dioxy and Ru is selected from H;

$X_1$ and $X_2$ are each selected from F (fluorine), Cl (chlorine), Br (bromine), or I (iodine), independently;

$X_A^-$ is monovalent acid radical ion.

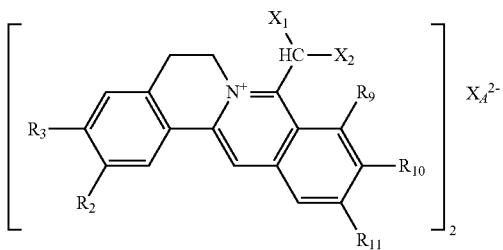

II when $R_2$ and $R_3$ are linked to form alkylene-dioxy, $R_9$ and $R_{10}$ are linked to form alkylene-dioxy and $R_{11}$ is selected from H;

or when $R_2$ and $R_3$ are linked to form alkylene-dioxy, $R_9$, $R_{10}$, and $R_{11}$ are selected from H, OH, or C1-C4 alkoxy, independently;

or when $R_2$ and $R_3$ are selected from H, OH, or C1-C4 alkoxy, independently, $R_9$ and $R_{10}$ are linked to form alkylene-dioxy and $R_{11}$ is selected from H;

$X_1$ and $X_2$ are each selected from F (fluorine), Cl (chlorine), Br (bromine), or I (iodine), independently;

$X_A^{2-}$ is divalent acid radical ion.

Furthermore, the first aspect of the present invention also provides the chemical structure formulae of 8-dihalomethyl berberine-type quaternary ammonium salt compounds of quaternized imine-type structure with the natures of hypotoxicity and hydrophilicity which are shown as the following formulae I and II:

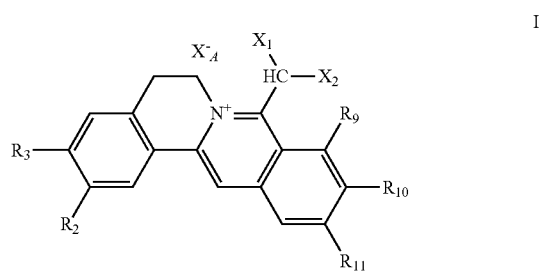

I

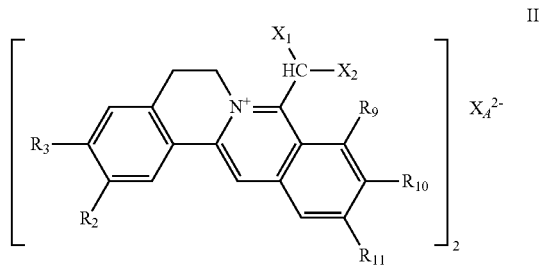

II

In general formulae I and II, $X_1$ and $X_2$ are selected from F (fluorine), Cl (chlorine), Br (bromine), or I (iodine), independently;

when $R_2$ and $R_3$ are linked to form alkylene-dioxy, $R_9$ and $R_{10}$ are linked to form alkylene-dioxy and $R_{11}$ is selected from H;

or when $R_2$ and $R_3$ are linked to form alkylene-dioxy, $R_9$, $R_{10}$ and $R_{11}$ are selected from H, OH, C1-C4 alkyl, C2-C4 alkanoyl, or C1-C4 alkoxy, independently; or when $R_2$ and $R_3$ are selected from H, OH, C1-C4 alkyl, C2-C4 alkanoyl, or C1-C4 alkoxy, independently, $R_9$ and $R_{10}$ are linked to form alkylene-dioxy and $R_{11}$ is selected from H;

$X_A^-$ is monovalent acid radical ion, and $X_A^{2-}$ is divalent acid radical ion.

In the present invention, said C1-C4 alkoxy are preferably selected from methoxy, ethoxy, propoxy, isopropoxy, and butoxy; said alkylene-dioxy are selected from methylenedioxy, ethylenedioxy, propylenedioxy, and butylenedioxy.

In the present invention, said C1-C4 alkyl are selected from methyl, ethyl, propyl, isopropyl, and butyl; and said C2-C4 alkanoyl are selected from acetoxy, propionyloxy, butyryloxy, and isobutyryloxy.

In general formula I, $X_A^-$ are monovalent inorganic acid radical ions or monovalent organic acid radical ions; the monovalent inorganic acid radical ions are selected from halide anions, hydrogen sulfate ion, hydrogen carbonate ion, dihydrogen phosphate ion, hypohalite ion (ClO$^-$), halite ion (ClO$_2^-$). halate ion radical (ClO$_3^-$), perhalate ion (ClO$_4^-$), and nitrate ion; the monovalent organic acid radical ions are selected from formate ion, acetate ion, propionate ion, benzoate ion, p-hydroxybenzoate ion, salicylate ion, protocatechuate ion, ferulate ion, isoferulate ion, homogentisate ion, cinnamate ion, p-hydroxycinnamate ion, caffeate ion, phenylacetate ion, 3-hydroxy-2-phenyl propionate ion (or tropate ion or phenylhydracrylate ion), gallate ion, veratrate ion, piperonylate, 3,4,5-trimethoxybenzoate ion, orsellinate ion, shikimate ion (3,4,5-trihydroxy-1-cyclohexene-1-carboxylate ion), (S)-lactate ion ((S)-2-hydroxy propionate ion), (R)-lactate ion ((R)-2-hydroxy propionate ion), (±)-lactate ion ((±)-2-hydroxy propionate ion), (2R,3R)-(+)-hydrogen tartarate ion, (2S,3S)-(−)-hydrogen tartarate ion, (±)-hydrogen tartarate ion, furoate ion. dihydrogen citrate ion, dihydrogen hydroxycitrate ion, hydrogen maleate ion, hydrogen fumarate ion, L-hydrogen malate ion, D-hydrogen malate ion, (dl)-hydrogen malate ion, hydrogen oxalate ion, hydrogen propanedioate ion, hydrogen glutarate ion, hydrogen adipate ion, hydrogen pimelate ion, hydrogen suberate ion, hydrogen azelaate ion, hydrogen sebacate ion, benzenesulfonate ion, gluconate ion, and ascorbate ion. Further, said monovalent organic acid radical ions can be selected from sulfamate ion, tosylate ion, methanesulfonate ion, ethanesulfonate ion, 2-naphthalenesulphonate ion, dichloroacetate ion, and difluoroacetate ion.

In general formula II, $X_A^2$ are divalent inorganic acid radical ions or divalent organic acid radical ions; the divalent inorganic acid radical ions are selected from sulfate ion, carbonate ion, and hydrogen phosphate ion; the divalent organic acid radical ions are selected from (2R,3R)-(+)-tartarate ion, (2S,3S)-(−)-tartarate ion, (±)-tartarate ion, hydrogen citrate ion, hydrogen hydroxycitrate ion, maleate ion, fumarate ion, L-malate ion, D-malate ion, (dl)-malate ion, oxalate ion, propanedioate ion, glutarate ion, adipate ion, pimelate ion, suberate ion, azelaate ion, and sebacate ion. Further, said divalent organic acid radical ions can be selected from benzenesulfonate ion with S→O dipolar bond, and benzoate ion with 2-oxygen anion.

The compounds of the present invention are selected from the group consisting of:

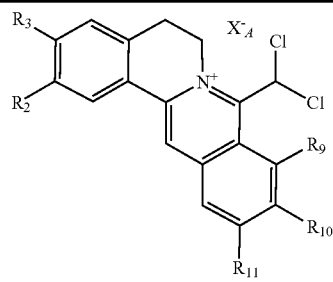

| | $R_2$ | $R_3$ | $R_9$ | $R_{10}$ | $R_{11}$ | $X_A^-$ |
|---|---|---|---|---|---|---|
| 1 | —OCH$_2$O— | | —OCH$_2$O— | | H | Cl$^-$ |
| 2 | —OCH$_2$O— | | H | —OCH$_2$O— | | Cl$^-$ |
| 4 | —OCH$_2$O— | | OMe | OMe | H | Cl$^-$ |
| 6 | OMe | OMe | OMe | OMe | H | Cl$^-$ |

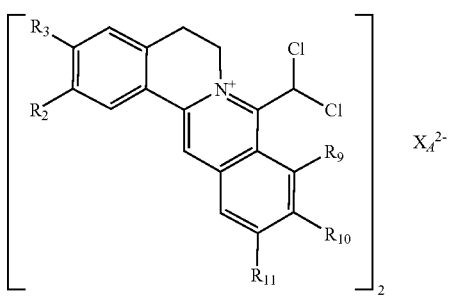

| | $R_2$ | $R_3$ | $R_9$ | $R_{10}$ | $R_{11}$ | $X_A^{2-}$ |
|---|---|---|---|---|---|---|
| 3 | —OCH$_2$O— | | H | —OCH$_2$O— | | [OOCCOO]$^{2-}$ |
| 5 | OMe | OMe | OMe | OMe | H | [SO$_4$]$^{2-}$ |

The most preferred compounds of the present invention are selected from the group consisting of:

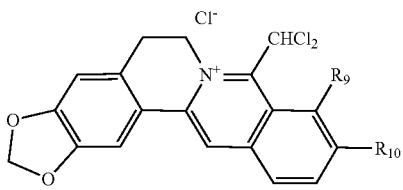

| | $R_9$ | $R_{10}$ |
|---|---|---|
| 1 | —OCH$_2$O— | |
| 3 | OMe | OMe |

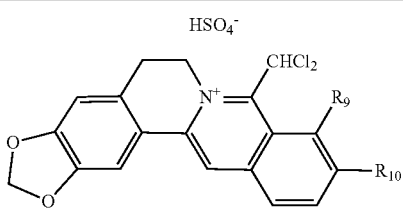

| | $R_9$ | $R_{10}$ |
|---|---|---|
| 5 | —OCH$_2$O— | |
| 7 | OMe | OMe |

-continued
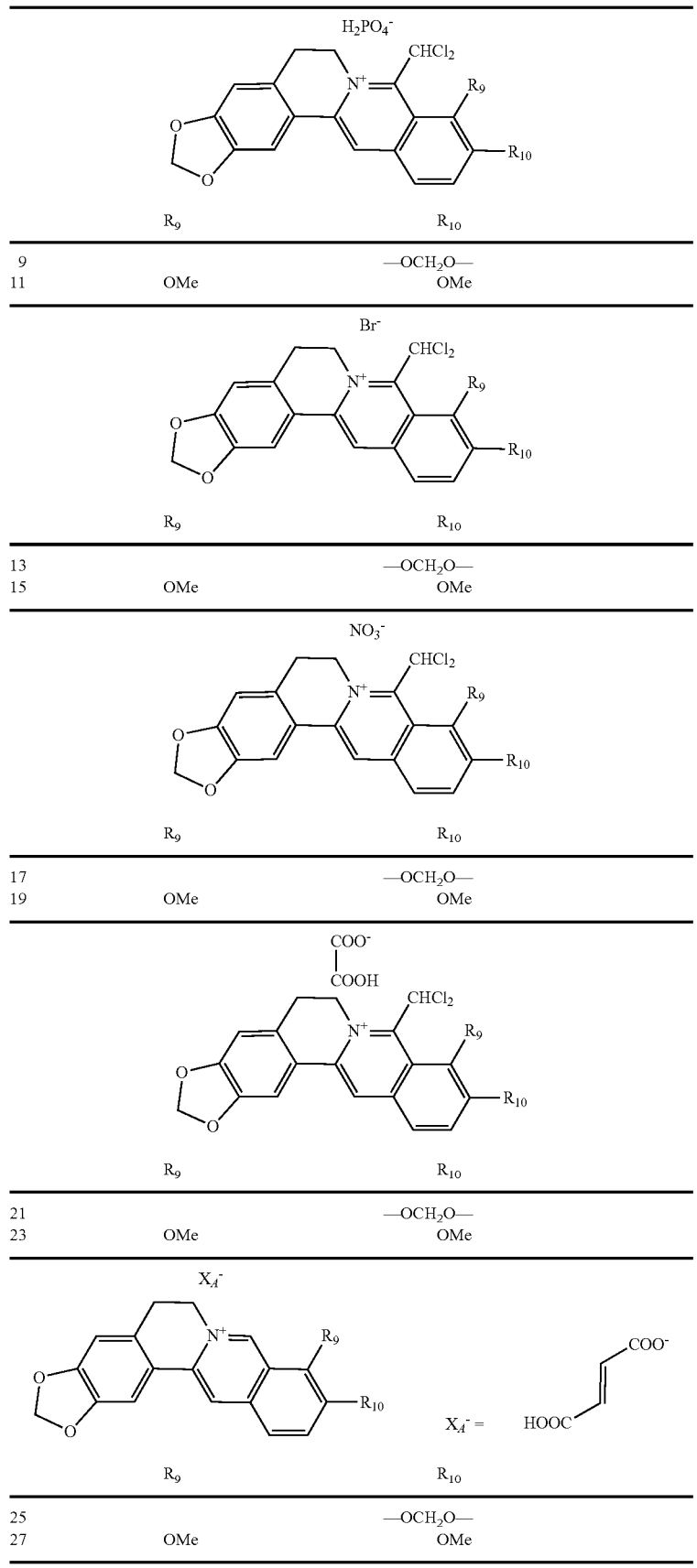
| R_9 | R_10 |
|---|---|
| 9 | —OCH_2O— |
| 11 OMe | OMe |
| 13 | —OCH_2O— |
| 15 OMe | OMe |
| 17 | —OCH_2O— |
| 19 OMe | OMe |
| 21 | —OCH_2O— |
| 23 OMe | OMe |
| 25 | —OCH_2O— |
| 27 OMe | OMe |

-continued

| | R₉ | R₁₀ |
|---|---|---|
| 29 | | —OCH₂O— |
| 31 | OMe | OMe |

| | R₉ | R₁₀ |
|---|---|---|
| 33 | | —OCH₂O— |
| 35 | OMe | OMe |

| | R₉ | R₁₀ |
|---|---|---|
| 37 | | —OCH₂O— |
| 39 | OMe | OMe |

| | R₉ | R₁₀ |
|---|---|---|
| 41 | | —OCH₂O— |
| 43 | OMe | OMe |

47

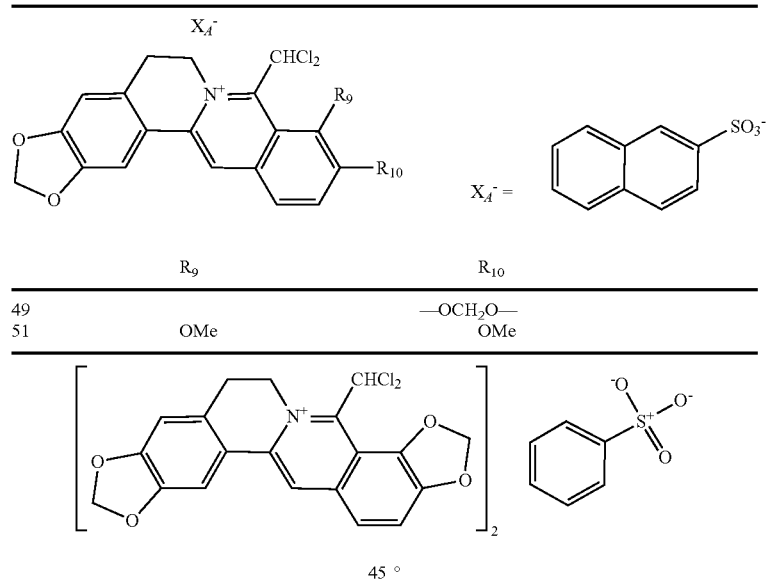

| | R_9 | R_10 |
|---|---|---|
| 49 | | —OCH_2O— |
| 51 | OMe | OMe |

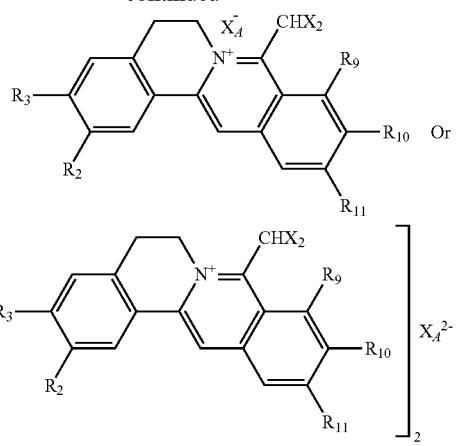

45 °

The second aspect of the present invention provides preparation methods of the compounds of the invention:

Said hypotoxic and hydrophilic 8-dihalomethyl berberine-type quaternary ammonium salt compounds of quaternized imine-type structure in the invention can be prepared by the following synthetic routes (Scheme 1; See the experimental examples of the invention for specific synthesis conditions):

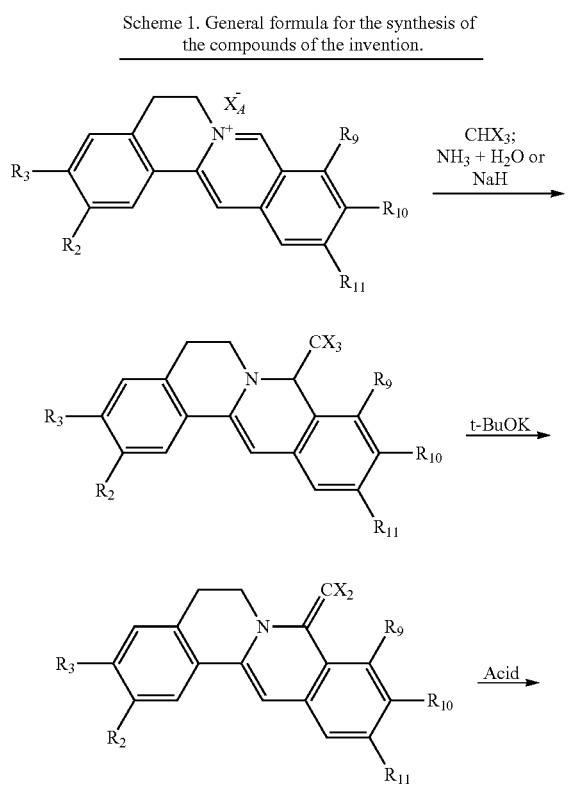

Synthesis procedure: (1) 8-trihalomethyl-dihydroberberine-type compounds were obtained by nucleophilic addition of nucleophilic reagents to substrates. The nucleophilic reagents are reactive species trihalomethyl anions which are obtained under alkaline conditions; (2) 8-dihalomethylene-dihydroberberine-type derivatives as key intermediates were obtained by elimination reaction of 8-trihalomethyl-dihydroberberine-type compounds under alkaline conditions; (3) 8-dihalomethyl berberine-type quaternary ammonium salt compounds of imine-type quaternized structures of the present invention are obtained through quaternization reaction of 8-dihalomethylene-dihydroberberine-type derivatives in the presence of various acids.

The third aspect of the present invention also relates to pharmaceutical compositions of hypotoxic and hydrophilic 8-dihalomethyl berberine-type quaternary ammonium salt compounds of quaternized imine-type structure claimed in the first aspect of the invention as active ingredients. The pharmaceutical composition can be prepared according to the methods known in various fields. It can be made into any forms of pharmaceutical preparation suitable for human or animal use via combining the compounds of the invention with one or more pharmaceutically acceptable solid or liquid excipients and/or adjuvants. The contents of the compounds of the present invention in the pharmaceutical compositions are generally 0.1-99.9% (W/W).

Compounds of the invention or pharmaceutical compositions containing the compounds of the invention may be administered in unit dose form. In view of the physical and chemical properties of the compounds of the invention, the administration route may be intestinal tract or non-intestinal tract, such as oral administration, intravenous injection, intramuscular injectino, subcutaneous injection, nasal administration, oral mucosa administration, eye administration, lung and respiratory tract administration, skin administration, vagina administration, rectum administration, and administration by coating on the diseased part of the skin, etc.

The drug dosage forms can be liquid dosage forms, solid dosage forms, or semi-solid dosage forms. Liquid dosage forms can be solution (including true solution and colloidal solution), emulsion (including O/W type, W/O type, and double emulsion), suspension, injection (including water injection, powder injection, and infusion), eye drops, nose drops, lotion, and liniment, etc. Solid dosage forms can be tablets (including ordinary tablets, enteric-coated tablets, lozenges, dispersible tablets, chewable tablets, effervescent tablets, and orally disintegrating tablets), capsules (including hard capsules, soft capsules, and enteric-coated capsules), granules, powders, pellets, dripping pills, suppositories, film agents, patches, gas (powder) aerosol, spray, and so on. Semisolid dosage forms can be ointments, cream type, gel, paste, and so on.

The compounds of the invention can be made into a common preparation, a slow-release preparation, a controlled-release preparation, a targeted preparation, and various microparticle administration systems.

In order to make the compounds of the invention into tablets, various excipients known in the related field can be widely used, including diluent, adhesive, wetting agent, disintegrating agent, lubricant, and flow aid. Diluent can be starch, dextrin, sucrose, glucose, lactose, mannitol, sorbitol, xylitol, microcrystalline cellulose, calcium sulfate, calcium hydrophosphate, and calcium carbonate, etc. The wetting agent can be water, ethanol, and isopropanol, etc. Adhesives can be starch, dextrin, syrup, honey, glucose solution, microcrystalline cellulose, arabic gum, gelatin, sodium carboxymethylcellulose, methylcellulose, hydroxypropylmethylcellulose, ethyl cellulose, acrylic resin, carbomer, polyvinylpyrrolidone, and polyethylene glycol, etc. Disintegrating agents can be dry starch, microcrystalline cellulose, low substituted hydroxypropyl cellulose, cross-linked polyvinylpyrrolidone, cross-linked carboxymethylcellulose sodium, carboxymethylstarch sodium, sodium bicarbonate and citric acid, polyoxyethylene sorbitol fatty acid ester, and sodium dodecyl sulfonate, etc. Lubricants and flow aids can be talcum powder, silica, stearate, tartaric acid, liquid paraffin, and polyethylene glycol, etc.

The tablets can also be further made into coated tablets, such as sugar coated tablets, film coated tablets, enteric coated tablets, or double-layer tablets and multi-layer tablets.

In order to make the administration unit into capsule, the active ingredients (compounds of the invention) can be mixed with diluent and flow aid, and the mixture can be directly placed into hard capsule or soft capsule. The active ingredients (compounds of the invention) can also be made into particles or pellets with diluents, adhesives, and disintegrating agents, and then placed into hard or soft capsules. All the diluents, adhesives, wetting agents, disintegrating agents, and flow aids used for preparing the tablets of the compounds of the invention can also be used for preparing the capsules of the compounds of the invention.

In order to make the compounds of the invention into an injection, water, ethanol, isopropanol, propylene glycol or a mixture thereof can be used as a solvent, and appropriate amount of commonly used solubilizers, cosolvents, pH regulators, and osmotic pressure regulators in pharmaceutical field can be added. The solubilizers or cosolvents may be poloxamer, lecithin, and hydroxypropyl-$\beta$-cyclodextrin, etc. The pH regulators can be phosphate, acetate, hydrochloride, and sodium hydroxide, etc. Osmotic pressure regulators can be sodium chloride, mannitol, glucose, phosphate, and acetate, etc. When preparing freeze-dried powder injection, mannitol and glucose can be added as proppant.

In addition, colorants, preservatives, fragrances, flavoring agents or other additives can also be added to pharmaceutical preparations if necessary.

In order to achieve the purpose of medication and enhance the therapeutic effect, the medicines or pharmaceutical compositions of the invention can be administered and used by any well-known administration method and application mode.

The drug administration (application) or medication (use) dose of the pharmaceutical composition of the compounds of the invention can be changed in a wide range according to the nature and severity of microbial infection, inflammation, ulcerative colitis or tumor to be prevented or treated, the individual conditions of patients or animals, the route of administration (application) and dosage forms etc. Generally speaking, the suitable daily dose range of the compounds of the invention is 0.001-300 mg/kg body weight, preferably 0.1-100 mg/kg, more preferably 1-60 mg/kg, most preferably 2-30 mg/kg. The above dosage can be taken in one dosage unit or in several dosage units, which depends on the doctor's clinical experience and the progress of treatment as well as administration (use) plan(s) including using other treatment (application) means.

The compounds or compositions of the invention can be taken alone or used in combination with other therapeutic drugs or symptomatic drugs. When the compounds of the invention have synergistic effect with other therapeutic drugs, the dosages should be adjusted according to the actual situation.

The forth aspect of the present invention provides a use of hypotoxic and hydrophilic 8-dihalomethyl berberine-type quaternary ammonium salt compounds of quaternized imine-type structure as shown in general formulae I and II to prepare drugs to prevent, relieve and/or treat microbial infections. Said microorganisms are selected from bacteria and fungi, and said bacteria are selected preferably from gram positive and gram negative bacteria.

The fifth aspect of the present invention provides a use of hypotoxic and hydrophilic 8-dihalomethyl berberine-type quaternary ammonium salt compounds of quaternized imine-type structure as shown in general formulae I and II to prepare drugs to prevent, relieve and/or treat inflammations.

The sixth aspect of the present invention provides a use of hypotoxic and hydrophilic 8-dihalomethyl berberine-type quaternary ammonium salt compounds of quaternized imine-type structure as shown in general formulae I and II to prepare drugs to prevent, relieve and/or treat ulcerative colitis.

The seventh aspect of the present invention provides utility of hypotoxic and hydrophilic 8-dihalomethyl berberine-type quaternary ammonium salt compounds of quaternized imine-type structure as shown in general formulae I and II to prepare drugs to prevent, relieve and/or treat tumors, especially in the prevention, mitigation and/or treatment of colorectal cancer, liver cancer, lung cancer, breast cancer, osteosarcoma, and glioma.

BENEFICIAL TECHNICAL EFFECTS

Based on the investigation and evaluation of physical and chemical indices and biological indices, it was shown that the compounds of the present invention have obvious hydrosolubility and alcohol solubility and significant medicinal effectiveness, safety, and quality stability. Therefore, the application prospect in the pharmaceutical field is very broader.

As compared with the corresponding quaternary ammonium salt substrates of berberine-type alkaloids, in addition to the significant increase in solubility in polar organic solvents such as methanol and ethanol, the hydrophilicity of the compounds of the present invention is also very obvious. The water solubility was determined at an ambient temperature of 25° C.±2° C. The amount of compounds 1, 3, 21, 23, 25, 27, 29, 31, 45, and 47 dissolved in each milliliter of water was as follows: 8-dichloromethyl coptisine hydrochloride (1) 5 mg, 8-dichloromethyl berberine hydrochloride (3) 35 mg, 8-dichloromethyl coptisine hydrogen oxalate (21) 5.25 mg, 8-dichloromethyl berberine hydrogen oxalate (23) 5.1 mg, 8-dichloromethyl coptisine hydrogen maleate (25) 3.71 mg, 8-dichloromethyl berberine hydrogen maleate (27) 3.83 mg, 8-dichloromethyl coptisine tosylate (29) 1.5 mg, 8-dichloromethyl berberine tosylate (31) 5.0 mg, bis(8-dichloromethyl coptisine) benzenesulfonate (with S→O dipolar bond) (45) 8.9 mg, and 8-dichloromethyl berberine benzenesulfonate (47) 6.45 mg, respectively. In parallel determination, the amount of coptisine hydrochloride and berberine hydrochloride as quaternary ammonium salt substrates of berberine-type alkaloid that can be dissolved in each milliliter of water is less than 1 mg and 2 mg, respectively.

The compounds of the invention have significant antimicrobial infection activity. As compared with the corresponding quaternary ammonium salt substrates of berberine-type alkaloids, the compounds of the invention have significantly stronger antibacterial activity against *Staphylococcus aureus* (*S. aureus*) and *Candida albicans* (*C. albicans*). In the parallel experiment, the minimum inhibitory concentration (MIC) of coptisine hydrochloride and berberine hydrochloride, as the quaternary ammonium salt substrates of berberine-type alkaloids, to *Staphylococcus aureus* and *Candida albicans* were more than 250 μg/ml and 125 μg/ml as well as 250 μg/ml and 250 μg/ml, respectively. The MIC of the compounds of the invention 8-dichloromethyl coptisine hydrochloride (1) and 8-dichloromethyl berberine hydrochloride (3) to *S. aureus* is 15.6 μg/ml and 31.2 μg/ml, respectively. The MIC of the compounds of the invention 8-dichloromethyl coptisine hydrochloride (1) and 8-dichloromethyl berberine hydrochloride (3) to *C. albicans* is 0.78 μg/ml and 3.9 μg/ml, respectively. Compound 1 showed the strongest antimicrobial activity, the MIC to *C. albicans* was 320 times higher than that of coptisine hydrochloride. In addition, the antibacterial ability of compound 1 of the invention against Gram-negative bacteria is significantly higher than that of its substrate, and the MIC to *Escherichia coli* is 62.5 μg/ml. Although the action intensity of the compounds of the invention against *S. aureus* and *E. coli* is lower than that of positive control levofloxacin in MIC evaluation, since the compounds of the invention are non-toxic and hypotoxic bioactive compounds, they have a broader application prospect even than levofloxacin. And the intensity of pharmacological action of the compounds of the invention against *C. albicans* is significantly higher in MIC evaluation than that of the positive control levofloxacin (the MIC of levofloxacin is more than 250 μg/ml). Therefore, using the compounds with dihalomethyl introduced into the C-8 position of the quaternary ammonium salt substrates of berberine-type alkaloids which were discovered in the present invention, the hydrophilicity can be significantly increased under the premise of no significant change in molecular volume and molecular weight, and the antimicrobial activity of these compounds can be greatly improved. This is different from the rule that the introduction of lipophilic groups can enhance the antibacterial activity of the quaternary ammonium salt of berberine-type alkaloids, which has been found in the disclosed data. In addition, there is no information about improving the antibacterial activity by enhancing the hydrosolubility of the protoberberine-type alkaloids in the disclosed data. The invention proved that the research for the purpose of enhancing the anti-microbial ability of the protoberberine-type alkaloids can be realized not only by improving the liposolubility, but also by improving the hydrosolubility, which is a new discovery with substantive progress.

In the whole animal experiment of anti-inflammatory activity, which was carried out by modeling and using the acute ear swelling model induced by croton oil, the therapeutic effect was evaluated by the inhibition rate of the compounds on the swelling degree of the focus in the experimental animal after treatment {Inhibition rate(%)= [(swelling degree of model group−swelling degree of administration group)/swelling degree of model group]×100 (%)}, the results showed that the compounds of the invention have significant anti-inflammatory activity. Under the dosage of 100 mg/kg, the anti-inflammatory effects of the compounds of the invention were significantly higher than that of the positive control compound indomethacin. Among them, it was found in the observation on curative effect at the end of the experiment that the inhibition rate of the inflammatory swelling degree of the invention compound 8-dichloromethyl coptisine hydrochloride (1) reached 56.59%[##] ([##], $P<0.01$, compared with the model group) when the dosage is 100 mg/kg. Compared with the inhibition rate 26.01%[#] of the positive control drug ([#], $P<0.05$, compared with the model group) against swelling degree, the efficacy was significantly improved. Although the dosage of the compounds of the invention in the experiment was greater than 5 mg/kg of the positive control drug indomethacin, also in view of the facts that the compounds of the invention have the prominent features of being non-toxic or hypotoxic bioactive compounds and the compounds of the invention are not homologous compound of indomethacin, and, considering the effectiveness and safety of drugs comprehensively (drug research cannot only consider the intensity of pharmacological action, the safety of drugs is even more important), the fact that in the case of large dosage of the compounds of the invention, the anti-inflammatory effect was stronger than that of the positive control drug and the experimental animal can endure high doses of the compounds of the invention just demonstrated that the compounds of the invention have more application value than the positive control drug in the preparation of drugs for preventing, alleviating and/or treating inflammation.

In the whole animal experiment of anti-ulcerative colitis by taking acute ulcerative colitis animal model, the therapeutic effect was evaluated by the percentage of body weight change of the experimental animals after treatment, the percentage of colonic contracture, and the effect on the disease activity index (DAI) and on the inhibition rate of DAI of model mice with ulcerative colitis. The results of each index indicated that the compounds of the invention have significant anti-ulcerative colitis activity. At a dose of 100 mg/kg, the activity intensity of the compounds of the invention against ulcerative colitis is significantly higher than the therapeutic effect of 500 mg/kg dose of the positive control drug salazosulfapyridine (SASP). Among them, it was found through observing curative effect at the end of the experiment that the body weight loss percentage of the animals in the administration group of the compounds of the invention 8-dichloromethyl coptisine hydrochloride (1) and 8-dichloromethyl berberine hydrochloride (3) was 8.19%$^{\#\#\#}$ and 25.54%, respectively ($^{\#\#\#}$P<0.01, compared with the model group) compared with the body weight at the beginning of the experiment when all the dosage was 100 mg/kg, while, the body weight loss percentage of the model group handled in parallel was 27.61% (P<0.01, compared with the normal control group). The percentage of colon contracture of compound 1 and compound 3 administration groups of the invention, compared to the length of colon in the normal control group, were 16.37%$^{\#\#}$ and 28.83%$^{\#}$ ($^{\#}$P<0.05, $^{\#\#}$P<0.01, compared with the model group), respectively, while the percentage of colon contracture in the model group was 36.34% (P<0.01, compared with the normal control group). The DAI inhibition rate values of compounds 1 and 3 administration groups of the invention reached 65.17%$^{\#\#}$ and 51.00%$^{\#\#}$, respectively ($^{\#\#}$P<0.01, compared with the model group), while the DAI inhibition rate of model group was 0%. Compared with the corresponding percentage 27.70% of body weight loss compared to the animal body weight at the beginning of the experiment, the percentage of colon contracture 28.43%$^{\#}$ ($^{\#}$P<0.05, compared with the model group) compared to the length of colon in the normal control group, and the DAI inhibition rate 23.33%$^{\#}$ ($^{\#}$P<0.05, compared with the model group) when the dosage of positive control SASP was 500 mg/kg, the curative effect was significantly higher. And the therapeutic effect of 8-dichloromethyl coptisine hydrochloride (1) was significantly improved compared with the corresponding experimental data of 18.77%$^{\#}$, 23.93%$^{\#\#}$, 44.03%$^{\#\#}$ ($^{\#}$P<0.05, $^{\#\#}$P<0.01, compared with the model group) of percentage of animal body weight loss, percentage of colon contracture compared to colon length in the normal control group, and DAI inhibition rate of the active compound dihydrocoptisine under the same dosage of 100 mg/kg.

Another important feature of the present invention is that it was clarified that the compounds of the invention have different regulatory effects on different target molecules related to tumorigenesis in different tumor cells. In the experiment, the tumor cells examined included colorectal cancer, liver cancer, lung cancer, breast cancer, osteosarcoma, and glioma cells, and the target molecules included STAT3, NF-κB, E-Cadherin, and PCNA.

The experimental results in C6 glioma cells showed that, compared to model group, compounds 1 and 3 significantly promoted the expression of E-cadherin protein, inhibited the expression of NF-κB. Compound 3 could inhibit the expression of PCNA. However, the inhibitory activity of compounds 1 and 3 on pSTAT3 was not detected in C6 cells.

The experimental results in human colon cancer cell line HCT116 showed that, compared to model group, compounds 1 and 3 had significant inhibitory effect on pSTAT3, also significant inhibitory activity on NF-κB. However, compounds 1 and 3 had less significant effect on the expression of E-cadherin and PCNA.

The experimental results in human large cell lung cancer cell line NCIH460 showed that, compared to model group, compound 1 could significantly promote the expression of E-cadherin, and compounds 1 and 3 not only obviously inhibited the expression of pSTAT3, but also obviously inhibited the expression of NF-κB. However, compounds 1 and 3 had less significant effect on PCNA expression.

The experimental results in human hepatoma cell line 7721 showed that, compared to model group, compounds 1 and 3 had very significant inhibitory effect on the expression of NF-κB. However, compounds 1 and 3 had less significant effect on the expression of E-cadherin.

The experimental results in human osteosarcoma cell line MG63 showed that, compared to model group, compounds 1 and 3 both significantly inhibited the expression of pSTAT3 and NF-κB.

The experimental results in human breast cancer cell MDA-MB-231 showed that, compared to model group, compounds 1 and 3 significantly inhibited the expression of pSTAT3, and compounds 1 and 3 both had obvious inhibitory effect on the expression of NF-κB. However, compounds 1 and 3 showed less significant effect on PCNA and E-cadherin. Through experimental study on tumorigenesis-related targets, it was confirmed that the compounds of the invention exhibited significant regulatory effect on target molecules closely related to tumorigenesis in vitro (involving apoptosis, tumor angiogenesis, invasion, and metastasis, etc.).

The compounds of the invention can achieve the curative effect of treating colorectal cancer and has significant effect. In the whole animal experiment which was carried out by modeling and using colorectal cancer animal model, the therapeutic effect was evaluated by spleen weight and calculated colon tumor burden of experimental animals as inspection indices after treatment. The results of each index indicated that the compounds of the invention have significant anti-colorectal cancer activity. At a dose of 50 mg/kg, the efficacy intensity of the compounds of the invention against malignant colorectal cancer was significantly higher than that of the positive control drug capecitabine at a dose of 250 mg/kg. Among them, it was found through observing the curative effect at the end of the experiment that, compared with the calculated value of tumor burden in normal control group (0.00), the tumor burden of mice in colorectal cancer model group increased significantly, the relative calculated value was 32.76±8.17, statistically showing significant difference (, p <0.01, compared with the normal control group). The positive drug capecitabine did not inhibit the increased tumor burden in colorectal cancer model mice at the dose of 250 mg/kg, the relative calculation value of tumor burden in mice was 42.69±10.26, significant difference in statistics not being observed. The compound 1 administration group of the invention had a significant inhibit effect on the tumor bueden increase of the colorectal cancer model mice at a dose of 50 mg/kg, showing the decrease of tumor number and tumor volume (including adenoma and adenocarcinoma) in the whole colon, the relative calculation value of tumor burden being 1.13±1.000$^{\#\#}$, and the statistical difference being very significant when compared with colorectal cancer model group ($^{\#\#}$, p<0.01). Therefore, the compounds of the invention have significant anti-colorectal cancer effect, and the effect of compound 1 of the invention is very significant compared with the positive control drug.

The compounds of the invention are nontoxic or hypotoxic specific anti-tumor compounds. These compounds are very valuable compounds in the prevention, remission and/or treatment of tumor diseases related to STAT3, NF-κB, E-cadherin signaling pathway and PCNA, and further in the prevention, remission and/or treatment of diseases related to colorectal cancer, liver cancer, lung cancer, breast cancer, osteosarcoma, and glioma.

In addition to the outstanding features that the hydrosolubility and pharmacological activity of the compounds of the invention were significantly improved and the improvement of hydrosolubility can also improve the antibacterial activity of the substrate, which was determined for the first time in the experiment of the invention, according to the research on the specificity of pharmacological action, another prominent feature of the compounds of the invention is that these compounds have the advantages of nontoxicity or hypotoxicity as well. In the test of toxicity (cell survival rate) of compounds 1 and 3 on 293T cells of human normal cell line cultured in vitro, the inhibition rates of compounds 1 and 3 on the growth of normal cells were 8.54% and −3.18%, respectively. In the acute toxicity experiment on Kunming mice (18-22 g), the $LD_{50}$ values of the compounds of the invention 8-dichloromethyl coptisine hydrochloride (1) and 8-dichloromethyl berberine hydrochloride (3) were more than 5.0 g/kg and 600 mg/kg, respectively, belonging to specific antibacterial, anti-inflammatory, anti-ulcerative colitis, and anti-tumor compounds with hypotoxicity or nontoxicity.

DESCRIPTION OF DRAWINGS

FIGS. 1A-F. Regulation effects of the compounds of the invention 1 and 3 on the protein expression of target molecules STAT3, NF-κB, PCNA, and E-Cadherin related to tumorigenesis in glioma cell C6, human colon cancer cell line HCT116, human lung cancer cell NCIH460, human hepatoma cell 7721, human osteosarcoma cell MG63, and human breast cancer cell MDA-MB-231.

EMBODIMENTS OF THE INVENTION

Figure 2:
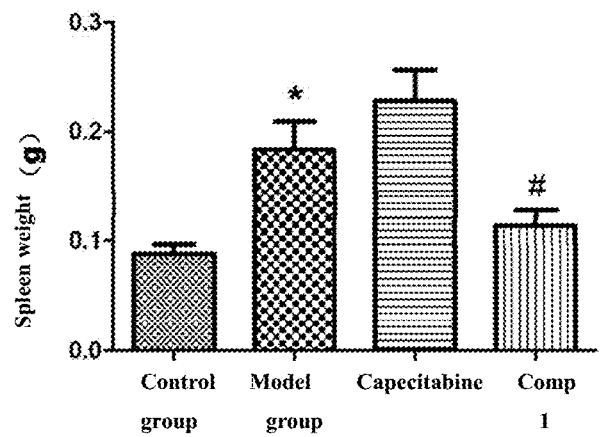
FIG. 2. Effect of the invention compound 1 on spleen weight of colorectal cancer model mice (*, p<0.05 versus control group; #, p<0.05 versus model group). Pos: Capecitabine FIG. 3. Effect of the invention compound 1 on colorectal tumor burden of colorectal cancer model mice (**, p<0.01 versus control group; ##, p<0.01 versus model group). Pos: Capecitabine

The specific embodiments of the invention do not limit the present invention in any way.

The preparation process and structure identification data of the active compounds of the present invention. Wherein, the compound numbers correspond to the specific compound numbers in the invention content.

1. Examples of the Preparation of Compounds in the Invention

Example 1. Preparation Process and Structure Identification Data of Compound 1

Dissolving coptisine hydrochloride (2.0 g, 5.62 mmol) in 200 ml mixed chloroform-methanol (3:1) solvent in reaction bottle and adding 24 ml concentrated ammonia water, the reaction was carried out under stirring at room temperature for 24 h. Then the chloroform layer was separated, washed using water twice, dried with anhydrous $MgSO_4$, and filtered. After evaporating the filtrate to dryness, the residue was purified using silica gel column chromatography eluted using dichloromethane, concentrating the eluate to obtain light yellow solid 8-trichloromethyl dihydrocoptisine of 617 mg (yield 25.0%). $^1$H NMR (500 MHz, $CDCl_3$) δ: 2.63-2.78 (m, 1H, $NCH_2CH_2$), 3.35 (m, 1H, $NCH_2CH_2$), 3.71 (m, 1H, $NCH_2CH_2$), 3.78-3.90 (m, 1H, $NCH_2CH_2$), 5.42 (s, 1H, CH—$CCl_3$), 5.91 (br, 1H, $OCH_2O$), 5.95 (br, 2H, $OCH_2O$), 6.02 (br, 2H, $OCH_2O$, C=CH), 6.61 (s, 1H, ArH), 6.67 (d, J=8.0 Hz, 1H, ArH), 6.86 (d, J=8.0 Hz, 1H, ArH), 7.16 (s, 1H, ArH). Weighing and dissolving 8-trichloromethyl dihydrocoptisine (585 mg, 1.33 mmol) in the mixed solvent of 10 ml t-BuOH and 10 ml DMSO in the reaction bottle, adding in t-BuOK (761 mg, 6.65 mmol), and rising temperature to 80° C. by oil bath on magnetic stirrer, the reaction mixture was reacted for 1.5 h under stirring, with the reaction process being detected by TLC until the reaction was completed. Concentrating the reaction mixture to remove most of the solvents under reduced pressure, ice water was added to the solution until the precipitation was complete. The solution was filtered under reduced pressure to obtain filter cake. The filter cake was washed using water until it was neutral, the filter cake was dried by airing and recrystallized with ethyl acetate to yield 8-dichloromethylene dihydrocoptisine yellow solid 115 mg in yield 21.4%. $^1$H NMR (500 MHz, DMSO-$d_6$) δ: 3.01 (br, 2H, $NCH_2CH_2$), 3.60 (br, 2H,$NCH_2CH_2$), 6.03 (s, 2H, $OCH_2O$), 6.07 (s, 2H,$OCH_2O$), 6.66 (s, 1H, ArCH=C), 6.77 (d, J=8.0 Hz, 1H, ArH), 6.82 (s, 1H, ArH), 7.00 (d, J=8.0 Hz, 1H, ArH), 7.43 (s, 1H, ArH); $^{13}$C NMR (100 MHz, DMSO-$d_6$) δ: 29.1, 47.1, 98.9, 100.7, 101.1, 103.5, 105.8, 108.38, 108.44, 109.6, 116.1, 122.6, 128.4, 129.7, 134.8, 137.1, 141.3, 145.8, 146.4, 147.3; ESI-MS (m/z): 402.0 [M+H]$^+$. Placing 8-dichloromethylene dihydrocoptisine (100 mg, 0.25 mmol) into the reaction bottle and adding in the methanol solution containing 10% hydrochloric acid 8 ml, the reaction mixture was heated to reflux and the reaction was stopped after 2 hours. The reaction solution was concentrated under reduced pressure to remove most of the solvent, and the residue was obtained. After diluting the residue with a small amount of water, suspending it and precipitating it completely, vacuum filtration was conducted. Washing the filter cake using a small amount of water and drying it via airing, a dark red solid of 8-dichloromethylcoptisine hydrochloride 94 mg was obtained in yield 86.8%. $^1$H NMR (500 MHz, $CD_3OD$) δ: 3.33 (br t-like, 2H, $NCH_2CH_2$), 5.34 (t, J=5.0 Hz, 2H, $NCH_2CH_2$), 6.13 (s, 2H, $OCH_2O$), 6.52 (s, 2H, $OCH_2O$), 7.01 (s, 1H, ArH), 7.72 (s, 1H, ArH), 7.99 (d, J=9.0 Hz, 1H, ArH), 8.01 (d, J=9.0 Hz, 1H, ArH), 8.82 (s, 1H, $CHCl_2$), 8.97 (s, 1H, ArCH=C); $^{13}$C NMR (100 MHz, $CD_3OD$) δ: 27.6, 54.4, 63.3, 103.9, 105.8, 107.2, 108.9, 113.1, 122.2, 123.4, 125.3, 126.4, 132.9, 136.5, 142.5, 143.2, 148.0, 150.1, 150.7, 152.8; ESI-MS (m/z): 402.0 [M-Cl]$^+$.

Example 2. Preparation Process and Structure Identification Data of Compound 3

Dissolving berberine hydrochloride (2.0 g, 5.38 mmol) in 60 ml chloroform solvent in reaction bottle and adding in 24 ml concentrated ammonia water, the reaction was carried out under stirring at room temperature for 24 h. Then the chloroform layer was separated, washed using water twice, dried with anhydrous $MgSO_4$, and filtered. After evaporating the filtrate to dryness, the residue was obtained and purified using silica gel column chromatography eluted with dichloromethane. The eluate was concentrated to dryness to obtain light yellow solid 8-trichloromethyl dihydroberberine of 1.775 g (yield 78.9%). $^1$H NMR (500 MHz, CDCl$_3$) δ: 2.73 (d, J =15.5 Hz, 1H, NCH$_2$CH$_2$), 3.33 (m, 1H, NCH$_2$CH$_2$), 3.71 (m, 1H, NCH$_2$CH$_2$), 3.87 (ov, 4H, ArOCH$_3$, NCH$_2$CH$_2$), 3.94 (s, 3H, ArOCH$_3$), 5.65 (s, 1H, CH—CCl$_3$), 5.94 (s, 2H, OCH$_2$O), 6.08 (br s, 1H, C═CHAr), 6.61 (s, 1H, ArH), 6.87 (d, J=7.0 Hz, 1H, ArH), 6.97 (d, J=7.0 Hz, 1H, ArH), 7.17 (s, 1H, ArH). Weighing and dissolving 8-trichloromethyl dihydroberberine (814 mg, 1.79 mmol) in the mixed solvent of 15 ml t-BuOH and 15 ml DMSO in the reaction bottle, adding in t-BuOK (1.025 g, 8.95 mmol), and rising temperature to 80° C. by oil bath under stirring, the reaction mixture was reacted for 1.5 h under stirring, with the reaction process being detected by TLC until the reaction was completed. The reaction solution was concentrated under reduced pressure to remove most of the solvents. After adding ice water to the residue for suspension, vacuum filtration was carried out. The filter cake was washed to neutral with water, dried by airing and recrystallized with ethyl acetate to yield 8-dichloromethylene dihydroberberine light yellow solid 218 mg in yield 29.1%. $^1$H NMR (500 MHz, DMSO-d$_6$) δ: 2.76 (br, 1H, NCH$_2$CH$_2$), 3.31 (br, 1H, NCH$_2$CH$_2$), 3.46 (br, 1H, NCH$_2$CH$_2$), 3.73 (ov, 4H, ArOCH$_3$, NCH$_2$CH$_2$), 3.80 (s, 3H, ArOCH$_3$,), 6.03 (s, 2H, OCH$_2$O), 6.56 (s, 1H, ArCH═C), 6.82 (s, 1H,ArH), 6.92 (d, J=8.5 Hz, 1H, ArH), 7.10 (d, J=8.5 Hz, 1H, ArH), 7.43 (s, 1H, ArH); $^{13}$C NMR (125 MHz, DMSO-d$_6$) δ: 29.0, 46.5, 56.2, 60.8, 97.7, 101.0, 103.6, 108.4, 110.4, 114.6, 114.8, 117.6, 122.6, 128.3, 129.5, 135.9, 137.1, 144.3, 146.4, 147.3, 150.0; ESI-MS (m/z): 418.1 [M+H]+. Weighing and placing 8-dichloromethylene dihydrocoptisine (188 mg, 0.45 mmol) in the reaction bottle and adding in the methanol solution containing 10% hydrochloric acid 15 ml, the reaction mixture was heated to reflux and the reaction was carried out under stirring and stopped after 2 hours. The reaction solution was concentrated under reduced pressure to remove most of the solvent, and a small amount of water was added in the residue to dilute until the precipitation was complete, and then filtration was conducted under reduced pressure. Washing the filter cake with a small amount of water and drying it via airing, a dark red solid of 8-dichloromethyl-berberine hydrochloride 115 mg was obtained in yield 56.3%. $^1$H NMR (500 MHz, CD$_3$OD) δ: 3.32 (m, 2H, NCH$_2$CH$_2$), 4.15 (s, 3H, ArOCH$_3$), 4.17 (s, 3H, ArOCH$_3$), 5.37 (m, 2H, NCH$_2$CH$_2$), 6.12 (s, 2H, OCH$_2$O), 7.00 (s, 1H, ArH), 7.73 (s, 1H, ArH), 8.18 (d, J=9.0 Hz, 1H, ArH), 8.23 (d, J=9.0 Hz, 1H, ArH), 8.96 (s, 1H, CHCl$_2$), 9.40 (s, 1H, ArCH═C); $^{13}$C NMR (125 MHz, CD$_3$OD) δ: 26.6, 53.8, 56.9, 62.6, 62.9, 102.8, 106.3, 107.8, 120.5, 121.1, 124.8, 126.0, 126.6, 132.1, 136.0, 141.8, 143.7, 148.3, 148.9, 151.7, 154.5; ESI-MS (m/z): 418.1 [M-Cl]$^+$.

Example 3. Preparation Process and Structure Identification Data of Compound 5

8-Dichloromethylene dihydrocoptisine (100 mg, 0.249 mmol) was placed into the reaction bottle, then 1.5 ml 95% ethanol was added in and the mixture was well-mixed. The 98% concentrated sulfuric acid (41 μl, 0.745 mmol) was added into 0.4 ml water to dilute to dilute sulfuric acid solution. This dilute sulfuric acid solution was dropped into the aforementioned reaction bottle containing 8-dichloromethylene dihydrocoptisine and 95% ethanol solution under stirring condition. The reaction was carried out for 1 h under 80° C. oil bath under heating. The reaction mixture was cooled to room temperature. After full precipitation of product, filtration was conducted under reduced pressure. The filter cake was washed using a small amount of 95% ethanol. The filter cake was dried by airing to yield 8-dichloromethyl-coptisine hydrogen sulfate dark red solid 114 mg in yield 91.7% (Combined with the structural identification of 8-dichloromethyl-coptisine hydrogen maleate and 8-dichloromethyl-berberine hydrogen maleate, compound 5 was confirmed to be 8-dichloromethyl-coptisine hydrogen sulfate). $^1$H NMR (400 MHz, DMSO-d$_6$) δ: 9.20 (s, 1H, ArCH═C), 8.68 (s, 1H, CHCl$_2$), 8.17 (d, J=8.8 Hz, 1H, ArH), 7.98 (d, J=8.8 Hz, 1H, ArH), 7.84 (s, 1H, ArH), 7.16 (s, 1H, ArH), 6.57 (s, 2H, ArH), 6.20 (s, 2H, OCH$_2$O), 5.22 (t, 2H, J=5.6 Hz, NCH$_2$CH$_2$), 3.29 (t, 2H, J=6.0 Hz, NCH$_2$CH$_2$).

Example 4. Preparation Process and Structure Identification Data of Compound 7

8-Dichloromethylene dihydroberberine (5.5 g, 13.149 mmol) was weighed and placed into the reaction bottle, and 130 ml tetrahydrofuran was added in the reaction bottle and the mixture was well-mixed. 98% concentrated sulfuric acid (2.1 ml, 39.448 mmol) was added into 12 ml purified water to dilute to dilute sulfuric acid solution. This dilute sulfuric acid solution was added dropwise into the aforementioned reaction solution containing 8-dichloromethylene dihydroberberine and tetrahydrfuran solution. Then, the reaction mixture was reacted for 1.5 h under stiring and refluxing on 70° C. oil bath under heating. The reaction mixture was cooled to room temperature. After full precipitation of product, filtration was conducted under reduced pressure. The filter cake was washed using tetrahydrofuran until the filtrate was colourless. The filter cake was dried under vacuum to yield 8-dichloromethyl-berberine hydrogen sulfate red solid 6.20 g in yield 91.3% (Combined with the structural identification of 8-dichloromethyl-coptisine hydrogen maleate and 8-dichloromethyl-berberine hydrogen maleate, compound 7 was confirmed to be 8-dichloromethyl-berberine hydrogen sulfate). $^1$H NMR (500 MHz, DMSO-d$_6$) δ:9.22 (s, 1H, ArCH═C), 9.20 (s, 1H, CHCl$_2$), 8.33 (d, J=9.1 Hz, 1H, ArH), 8.15 (d, J=9.1 Hz, 1H, ArH), 7.86 (s, 1H, ArH), 7.16 (s, 1H, ArH), 6.21 (s, 2H, OCH$_2$O), 5.26 (t, J=6.0 Hz, 2H, NCH$_2$CH$_2$), 4.12 (s, 3H, ArOCH$_3$), 4.06 (s, 3H, ArOCH$_3$), 3.30 (t, J=6.0 Hz, 2H, NCH$_2$CH$_2$); $^{13}$C NMR (100 MHz, DMSO-d$_6$) δ: 153.38, 150.34, 147.66, 147.03, 142.61, 140.74, 134.86, 131.59, 126.67, 125.35, 124.50, 120.59, 119.84, 107.81, 106.02, 102.17, 62.83, 62.37, 57.24, 52.96, 25.79.

Example 5. Preparation Process and Structure Identification Data of Compound 9

8-Dichloromethylene dihydrocoptisine (100 mg, 0.249 mmol) was weighed and placed into the reaction bottle, and 8 ml 95% ethanol was added in the reaction bottle and the mixture was well-mixed. 85% phosphoric acid (230 3.735 mmol) was added in dropwise. Then, the reaction mixture was reacted for 2 h under stirring and refluxing on 80° C. oil bath under heating. The reaction mixture was cooled to room temperature. After full precipitation of product, filtration was conducted under reduced pressure. The filter cake was washed using tetrahydrofuran and a small amount of 95% ethanol solution. The filter cake was dried under vacuum to yield 8-dichloromethyl-coptisine dihydrogen phosphate dark red solid 116 mg in yield 93.3%. $^1$H NMR (500 MHz, CD3OD) δ: 8.97 (s, 1H, ArCH=C), 8.82 (s, 1H, CHCl$_2$), 7.99 (s, 2H, ArH), 7.71 (s, 1H, ArH), 7.01 (s, 1H, ArH), 6.52 (s, 2H, OCH$_2$O), 6.14 (s, 2H, OCH$_2$O), 5.34 (br t-like, 2H, NCH$_2$CH$_2$), ~3.30 (ov, 2H, NCH$_2$CH$_2$).

Example 6. Preparation Process and Structure Identification Data of Compound 11

8-Dichloromethylene dihydroberberine (200 mg, 0.478 mmol) was weighed and placed into the reaction bottle, and 20 ml 95% ethanol was added in the reaction bottle and the mixture was well-mixed. 85% phosphoric acid (440 μl, 7.172 mmol) was added in dropwise. Then, the reaction mixture was reacted for 1 h under stirring and refluxing on 80° C. oil bath under heating. The reaction mixture was cooled to room temperature. After full precipitation of product, filtration was conducted under reduced pressure. The filter cake was washed using tetrahydrofuran until the filtrate was colourless. The filter cake was dried under vacuum to yield 8-dichloromethyl-berberine dihydrogen phosphate red solid 130 mg in yield 52.7%. $^1$-H NMR (500 MHz, DMSO-d$_6$) δ: 9.21 (s, 1H, ArCH=C), 9.19 (s, 1H, CHCl$_2$), 8.33 (d, J=9.0 Hz, 1H, ArH), 8.14 (d, J=9.0 Hz, 1H, ArH), 7.85 (s, 1H, ArH), 7.16 (s, 1H, ArH), 6.21 (s, 2H, OCH$_2$O), 5.26 (t-like, 2H, NCH$_2$CH$_2$), 4.12 (s, 3H, ArOCH$_3$), 4.05 (s, 3H, ArOCH$_3$), 3.30 (t-like, 2H, NCH$_2$CH$_2$), ~4.88 (br, OH).

Example 7. Preparation Process and Structure Identification Data of Compound 13

8-Dichloromethylene dihydrocoptisine (200 mg, 0.497 mmol) was weighed and placed into the reaction bottle, and 8 ml 95% ethanol was added in the reaction bottle and the mixture was well-mixed. Then, hydrobromic acid (172 μl, 1.492 mmol) was added in dropwise. The reaction mixture was reacted for 1 h under stirring and refluxing on 80° C. oil bath under heating. The reaction mixture was cooled to room temperature. After full precipitation of product, filtration was conducted under reduced pressure. The filter cake was washed using tetrahydrofuran until the filtrate was colourless. The filter cake was dried under vacuum to yield 8-dichloromethyl-coptisine hydrobromate red solid 216 mg in yield 90.0%. $^1$H NMR (500 MHz, DMSO-d$_6$) δ: 9.22 (s, 1H, ArCH=C), 8.68 (s, 1H, CHCl$_2$), 8.17 (d, J=8.8 Hz, 1H, ArH), 8.00 (d, J=8.8 Hz, 1H, ArH), 7.85 (s, 1H, ArH), 7.16 (s, 1H, ArH), 6.57 (s, 2H, OCH$_2$O), 6.21 (s, 2H, OCH$_2$O), 5.22 (t-like, 2H, NCH$_2$CH$_2$), 3.29 (t-like, 2H, NCH$_2$CH$_2$); $^{13}$C NMR (100 MHz, DMSO-d$_6$) δ: 150.25, 148.44, 147.68, 145.59, 141.29, 140.32, 134.23, 131.33, 125.10, 123.60, 122.08, 120.73, 111.16, 107.84, 105.94, 104.13, 102.16, 61.79, 52.52, 25.67.

Example 8. Preparation Process and Structure Identification Data of Compound 15

8-Dichloromethylene dihydroberberine (200 mg, 0.478 mmol) was weighed and placed into the reaction bottle, and 6 ml 95% ethanol was added in the reaction bottle and the mixture was well-mixed. Then, hydrobromic acid (166 μl, 1.434 mmol) was added in dropwise. The reaction mixture was reacted for 1 h under stirring and refluxing on 80° C. oil bath under heating. The reaction mixture was cooled to room temperature. After full precipitation of product, filtration was conducted under reduced pressure. The filter cake was washed using tetrahydrofuran until the filtrate was colourless. The filter cake was dried under vacuum to yield 8-dichloromethyl-berberine hydrobromate red solid 185 mg in yield 77.5%. $^1$H NMR (500 MHz, DMSO-d$_6$) δ: 9.21 (s, 2H, ArCH=C, CHCl2), 8.33 (d, J=9.1 Hz, 1H, ArH), 8.15 (d, J=9.1 Hz, 1H, ArH), 7.86 (s, 1H, ArH), 7.16 (s, 1H, ArH), 6.21 (s, 2H, OCH$_2$O), 5.26 (t, J=6.0 Hz, 2H, NCH$_2$CH$_2$), 4.12 (s, 3H, ArOCH$_3$), 4.05 (s, 3H, ArOCH$_3$), 3.30 (t, J=6.0 Hz, 2H, NCH$_2$CH$_2$); $^{13}$C NMR (100 MHz, DMSO-d$_6$) 153.37, 150.34, 147.66, 147.03, 142.62, 140.74, 134.86, 131.59, 126.67, 125.32, 124.49, 120.60, 119.85, 107.81, 106.01, 102.17, 62.83, 62.37, 57.24, 52.97, 25.80.

Example 9. Preparation Process and Structure Identification Data of Compound 17

8-Dichloromethylene dihydrocoptisine (200 mg, 0.497 mmol) was weighed and placed into the reaction bottle, and 4 ml 95% ethanol solution was added in the reaction bottle and the mixture was well-mixed. The concentrated nitric acid (102 μl 1.492 mmol) was added into 1 ml water to dilute to dilute nitric acid solution and this dilute nitric acid solution was dropped into the reaction bottle. The reaction mixture was reacted for 1 h under stirring and refluxing on 80° C. oil bath under heating. The reaction mixture was cooled to room temperature. After full precipitation of product, filtration was conducted under reduced pressure. The filter cake was washed using tetrahydrofuran. The filter cake was dried under vacuum to yield 8-dichloromethyl-coptisine nitrate red crystal 187 mg in yield 80.8%. $^1$H NMR (400 MHz, DMSO-d$_6$) δ: 9.20 (s, 1H, ArCH=C), 8.68 (s, 1H, CHCl$_2$), 8.17 (d, J=8.8 Hz, 1H, ArH), 7.98 (d, J=8.8 Hz, 1H, ArH), 7.84 (s, 1H, ArH), 7.16 (s, 1H, ArH), 6.57 (s, 2H, OCH$_2$O), 6.21 (s, 2H, OCH2O), 5.22 (t, 2H, J=5.6 Hz, NCH$_2$CH$_2$), 3.30 (t, 2H, J=6.0 Hz, NCH$_2$CH$_2$).

Example 10. Preparation Process and Structure Identification Data of Compound 19

8-Dichloromethylene dihydroberberine (200 mg, 0.478 mmol) was weighed and placed into the reaction bottle, and 4 ml 95% ethanol was added in the reaction bottle and the mixture was well-mixed. The concentrated nitric acid (98 μl 1.434 mmol) was added into 1 ml water to dilute to dilute nitric acid solution and this dilute nitric acid solution was dropped into the reaction bottle. The reaction mixture was reacted for 1 h under stirring and refluxing on 80° C. oil bath under heating. The reaction mixture was cooled to room temperature. After full precipitation of product, filtration was conducted under reduced pressure. The filter cake was washed using tetrahydrofuran until the filtrate was colourless. The filter cake was dried under vacuum to yield 8-dichloromethyl-berberine nitrate red solid 184 mg in yield 80.0%. $^1$H NMR (400 MHz, DMSO-d$_6$) δ: 9.21 (s, 1H, ArCH=C), 9.19 (s, 1H, CHCl$_2$), 8.32 (d, J=9.2 Hz, 1H, ArH), 8.14 (d, J=9.2 Hz, 1H, ArH), 7.85 (s, 1H, ArH), 7.16 (s, 1H, ArH), 6.21 (s, 2H, OCH$_2$O), 5.26 (t, J=5.6 Hz, 2H, NCH$_2$CH$_2$), 4.12 (s, 3H, ArOCH$_3$), 4.05 (s, 3H, ArOCH$_3$), 3.33 (ov, 2H, NCH$_2$CH$_2$).

Example 11. Preparation Process and Structure Identification Data of Compound 21

Oxalic acid dihydrate (190 mg, 1.492 mmol) was weighed and placed into the reaction bottle, and 10 ml methanol was added in the reaction bottle and the mixture was well-mixed. 8-Dichloromethylene dihydrocoptisine (200 mg, 0.497 mmol) was added to the above solution batchwise. The reaction mixture was reacted for 1 h under stirring and refluxing on 80° C. oil bath under heating. The reaction mixture was cooled to room temperature. Most solvent was removed via concentration under reduced pressure. 4 ml water was added in. After full precipitation of product, filtration was conducted under reduced pressure. The filter cake was washed using tetrahydrofuran until the filtrate was colourless. The filter cake was dried under vacuum to yield 8-dichloromethyl-copyisine hydrogen oxalate dark red solid 237 mg in yield 96.8%. $^1$H NMR (400 MHz, DMSO-d$_6$) δ: 9.21 (s, 1H, ArCH=C), 8.68 (s, 1H, CHCl$_2$), 8.17 (d, J=8.8 Hz, 1H, ArH), 7.99 (d, J=8.8 Hz, 1H, ArH), 7.84 (s, 1H, ArH), 7.16 (s, 1H, ArH), 6.57 (s, 2H, OCH$_2$O), 6.21 (s, 2H, OCH$_2$O), 5.22 (t, 2H, J=5.6 Hz, NCH$_2$CH$_2$), 3.30 (t, 2H, J=6.0 Hz, NCH$_2$CH$_2$).

Example 12. Preparation Process and Structure Identification Data of Compound 23

Oxalic acid dihydrate (190 mg, 1.434 mmol) was weighed and placed into the reaction bottle, and 10 ml methanol was added in the reaction bottle and the mixture was well-mixed via stirring. Then, 8-dichloromethylene dihydroberberine (200 mg, 0.478 mmol) was added in batchwise and, after finishing, the reaction mixture was reacted for 1 h under stirring and refluxing on 80° C. oil bath under heating until the reaction was completed. The reaction mixture was cooled to room temperature. The solvent was concentrated under reduced pressure to dryness. 10 ml of water was added into the residue in the reaction bottle, and then the mixture was well-shaken and filtered under reduced pressure. The filter cake was washed using ether to yield 8-dichloromethyl-berberine hydrogen oxalate red solid 98 mg in yield 40.3%. $^1$H NMR (500 MHz, DMSO-d$_6$) δ: 9.21 (s, 1H, ArCH=C), 9.19 (s, 1H, CHCl$_2$), 8.33 (d, J=8.8 Hz, 1H, ArH), 8.14 (d, J=8.8 Hz, 1H, ArH), 7.85 (s, 1H, ArH), 7.16 (s, 1H, ArH), 6.21 (s, 2H, OCH$_2$O), 5.26 (br t-like, 2H, NCH$_2$CH$_2$), 4.12 (s, 3H, ArOCH$_3$), 4.05 (s, 3H, ArOCH$_3$), 3.30 (br t-like, 2H, NCH$_2$CH$_2$).

Example 13. Preparation Process and Structure Identification Data of Compound 25

Maleic acid (190 mg, 1.492 mmol) was weighed and placed into the reaction bottle, and 1 ml water and 10 ml 95% ethanol was added in the reaction bottle and the mixture was mixed up. Then, 8-dichloromethylene dihydrocoptisine (200 mg, 0.497 mmol) was added in batchwise and, after finishing, the reaction mixture was reacted for 2 h under stirring and refluxing on 80° C. oil bath under heating. The reaction mixture was cooled to room temperature. Most of the solvent was removed via concentrating under reduced pressure. 4 ml of tetrahydrofuran was added in the reaction mixture. After full precipitation of product, filtration was conducted under reduced pressure. The filter cake was washed using tetrahydrofuran until the filtrate was colourless. The filter cake was dried under vacuum to yield 8-dichloromethyl-coptisine hydrogen maleate red solid 208 mg in yield 80.7%. $^1$H NMR (400 MHz, DMSO-d$_6$) δ: 9.21 (s, 1H, ArCH=C), 8.68 (s, 1H, CHCl$_2$), 8.17 (d, J=8.8 Hz, 1H, ArH), 7.98 (d, J=8.8 Hz, 1H, ArH), 7.84 (s, 1H, ArH), 7.16 (s, 1H, ArH), 6.57 (s, 2H, OCH$_2$O), 6.21 (s, 2H, OCH$_2$O), 6.01 (s, 2H, HOOCCH=CHCOO$^-$), 5.22 (t, 2H, J=6.4 Hz, NCH$_2$CH$_2$), 3.30 (t, 2H, J=6.0 Hz, NCH$_2$CH$_2$).

Example 14. Preparation Process and Structure Identification Data of Compound 27

Maleic acid (166 mg, 1.434 mmol) was weighed and placed into the reaction bottle, and 10 ml methanol was added in the reaction bottle and the mixture was mixed up via stirring. Then, 8-dichloromethylene dihydroberberine (200 mg, 0.478 mmol) was added in batchwise and, after finishing, the reaction mixture was reacted for 1 h under stirring and refluxing on 80° C. oil bath under heating until the reaction was completed. The reaction mixture was cooled to room temperature. The solvent was evaporated under reduced pressure to dryness. 10 ml of water was added into the residue in the reaction bottle, and then well-shaken and filtered under reduced pressure. The filter cake was washed using ether to yield 8-dichloromethyl-berberine hydrogen maleate red solid 120 mg in yield 47.0%. $^1$H NMR (500 MHz, DMSO-d$_6$) δ: 9.21 (s, 1H, ArCH=C), 9.19 (s, 1H, CHCl$_2$), 8.32 (d, J=9.0 Hz, 1H, ArH), 8.14 (d, J=9.0 Hz, 1H, ArH), 7.85 (s, 1H, ArH), 7.16 (s, 1H, ArH), 6.21 (s, 2H, OCH$_2$O), 6.03 (s, 2H, HOOCCH=CHCOO$^-$), 5.26 (br t-like, 2H, NCH$_2$CH$_2$), 4.12 (s, 3H, ArOCH$_3$), 4.06 (s, 3H, ArOCH$_3$), 3.32 (ov, 2H, NCH$_2$CH$_2$).

Example 15. Preparation Process and Structure Identification Data of Compound 29

P-toluenesulfonic acid (p-TsOH, 128 mg, 0.746 mmol) was weighed and placed into the reaction bottle, and 8 ml methanol was added in the reaction bottle and the mixture was well-mixed. Then, 8-dichloromethylene dihydrocoptisine (100 mg, 0.249 mmol) was added in batchwise and, after finishing, the reaction mixture was reacted for 1 h under stirring and refluxing on 80° C. oil bath under heating. The reaction mixture was cooled to room temperature. Most solvent was removed via concentration under reduced pressure. 2 ml water was added in the reaction mixture. After full precipitation of product, filtration was conducted under reduced pressure. The filter cake was washed using tetrahydrofuran until the filtrate was colourless. The filter cake was dried under vacuum to yield 8-dichloromethyl-copyisine tosylate red solid 138 mg in yield 96.6%. $^1$H NMR (400 MHz, DMSO-d$_6$) δ: 9.20 (s, 1H, ArCH=C), 8.68 (s, 1H, CHCl$_2$), 8.16 (d, J=8.8 Hz, 1H, ArH), 7.98 (d, J=8.8 Hz, 1H, ArH), 7.84 (s, 1H, ArH), 7.47 (d, J=8.0 Hz, 2H, ArH), 7.15 (s, 1H, ArH), 7.10 (br d, J=8.0 Hz, 2H, ArH), 6.57 (s, 2H, OCH$_2$O), 6.20 (s, 2H, OCH$_2$O), 5.22 (t, 2H, J=6.4 Hz, NCH$_2$CH$_2$), 3.29 (t, 2H, J=6.0 Hz, NCH$_2$CH$_2$), 2.28 (s, 3H, ArCH$_3$).

Example 16. Preparation Process and Structure Identification Data of Compound 31

8-Dichloromethylene dihydroberberine (200 mg, 0.478 mmol) was weighed and placed into the reaction bottle, and 8 ml tetrahydrofuran was added in the reaction bottle and the mixture was well-mixed. Then, p-toluenesulfonic acid (p-TsOH, 247 mg, 1.434 mmol) was added in batchwise and, after finishing, the reaction mixture was reacted for 1 h under stirring and refluxing on 70° C. oil bath under heating. The reaction mixture was cooled to room temperature. Filtration was conducted under reduced pressure. The filter cake was washed using tetrahydrofuran until the filtrate was colourless. The filter cake was dried under vacuum to yield 8-dichloromethyl-berberine tosylate red solid 186 mg in yield 65.9%. $^1$H NMR (500 MHz, DMSO-d$_6$) δ: 9.21 (s, 1H, ArCH=C), 9.19 (s, 1H, CHCl$_2$), 8.32 (d, J=9.0 Hz, 1H, ArH), 8.14 (d, J=9.0 Hz, 1H, ArH), 7.85 (s, 1H, ArH), 7.47 (d, J=7.5 Hz, 2H, ArH), 7.16 (s, 1H, ArH), 7.11 (d, J=7.5 Hz, 2H, ArH), 6.21 (s, 2H, OCH$_2$O), 5.26 (br t-like, 2H, NCH$_2$CH$_2$), 4.12 (s, 3H, ArOCH$_3$), 4.05 (s, 3H, ArOCH$_3$), 3.30 (br t-like, 2H, NCH$_2$CH$_2$), 2.29 (s, 3H, CH$_3$ArSO$_3$).

Example 17. Preparation Process and Structure Identification Data of Compound 33

8-Dichloromethylene dihydrocoptisine (100 mg, 0.249 mmol) was weighed and placed into the reaction bottle, and 6 ml tetrahydrofuran was added in the reaction bottle and the mixture was well-mixed. Sulfamic acid (36 mg, 0.373 mmol) was weighed and dissolved with 1 ml DMSO. This sulfamic acid solution was added into the reaction solution dropwise and, after finishing, the reaction mixture was reacted for 2 h under stirring and refluxing on 70° C. oil bath under heating. The reaction mixture was cooled to room temperature. Filtration was conducted under reduced pressure. The filter cake was washed using tetrahydrofuran until the filtrate was colourless. The filter cake was dried under vacuum to yield 8-dichloromethyl-coptisine sulfamate red solid 110 mg in yield 88.6%. $^1$H NMR (500 MHz, DMSO-d$_6$) δ: 9.22 (s, 1H, ArCH=C), 8.68 (s, 1H, CHCl$_2$), 8.17 (d, J=8.6 Hz, 1H, ArH), 8.00 (d, J=8.6 Hz, 1H, ArH), 7.85 (s, 1H, ArH), 7.16 (br s, 3H, ArH, NH$_2$SO$_3^-$), 6.57 (s, 2H, OCH$_2$O), 6.21 (s, 2H, OCH$_2$O), 5.22 (br t-like, 2H, NCH$_2$CH$_2$), 3.29 (br t-like, 2H, NCH$_2$CH$_2$); HRMS(ESI) (m/z): C$_{20}$H$_{14}$O$_4$NCl$_2$ [M-NH$_2$SO$_3^-$]$^+$ calculated: 402.02944; discovered: 402.02994.

Example 18. Preparation Process and Structure Identification Data of Compound 35

8-Dichloromethylene dihydroberberine (100 mg, 0.239 mmol) was weighed and placed into the reaction bottle, and 5 ml absolute methanol was added in the reaction bottle and the mixture was well-mixed. Then, sulfamic acid (70 mg, 0.717 mmol) was added in batchwise and, after finishing, the reaction mixture was reacted for 1 h under stirring and refluxing on 80° C. oil bath under heating. The reaction mixture was cooled to room temperature. The solvent was evaporated under reduced pressure to dryness. 9 ml tetrahydrofuran was added in the reaction mixture to precipitate the product. Filtration was conducted under reduced pressure. The filter cake was washed using tetrahydrofuran until the filtrate was colourless. The filter cake was dried under vacuum to yield 8-dichloromethyl-berberine sulfamate red solid 114 mg in yield 92.5%. $^1$H NMR (500 MHz, DMSO-d$_6$) δ: 9.21 (s, 1H, ArCH=C), 9.20 (s, 1H, CHCl$_2$), 8.33 (d, J=9.2 Hz, 1H, ArH), 8.14 (d, J=9.2 Hz, 1H, ArH), 7.86 (s, 1H, ArH), 7.19 (br s, 2H, NH$_2$SO$_3^-$), 7.17 (s, 1H, ArH), 6.21 (s, 2H, OCH$_2$O), 5.26 (br t-like, 2H, NCH$_2$CH$_2$), 4.12 (s, 3H, ArOCH$_3$), 4.05 (s, 3H, ArOCH$_3$), 3.30 (t, J=6.0 Hz, 2H, NCH$_2$CH$_2$); $^{13}$C NMR (100 MHz, DMSO-d$_6$) δ: 153.37, 150.34, 147.66, 147.03, 142.61, 140.75, 134.86, 131.59, 126.67, 125.34, 124.49, 120.60, 119.85, 107.81, 106.01, 102.17, 62.83, 62.37, 57.23, 52.96, 25.79; HRMS(ESI) (m/z): C$_{21}$H$_{18}$O$_4$NCl$_2$[M-NH$_2$SO$_3$]$^+$ calculated: 418.06074; discovered: 418.06021.

Example 19. Preparation Process and Structure Identification Data of Compound 37

8-Dichloromethylene dihydrocoptisine (200 mg, 0.497 mmol) was weighed and placed into the reaction bottle, and 5 ml 95% ethanol was added in the reaction bottle and the mixture was well-mixed. Then, methanesulfonic acid (97 μl, 1.492 mmol) was added in batchwise and, after finishing, the reaction mixture was reacted for 1 h under stirring and refluxing on 80° C. oil bath under heating. The reaction mixture was cooled to room temperature and the product was precipitated. Filtration was conducted under reduced pressure. The filter cake was washed using tetrahydrofuran and diethyl ether anhydrous until the filtrate was colourless. The filter cake was dried under vacuum to yield 8-dichloromethyl-coptisine methanesulfonate red solid 224 mg in yield 90.4%. $^1$H NMR (400 MHz, DMSO-d$_6$) δ: 9.21 (s, 1H, ArCH=C), 8.68 (s, 1H, CHCl$_2$), 8.17 (d, J=8.8 Hz, 1H, ArH), 7.99 (d, J=8.8 Hz, 1H, ArH), 7.84 (s, 1H, ArH), 7.16 (s, 1H, ArH), 6.57 (s, 2H, OCH$_2$O), 6.21 (s, 2H, OCH$_2$O), 5.22 (t, 2H, J=5.6 Hz, NCH$_2$CH$_2$), 3.29 (t, 2H, J=6.0 Hz, NCH$_2$CH$_2$), 2.29 (s, 3H, CH$_3$SO$_3^-$).

Example 20. Preparation Process and Structure Identification Data of Compound 39

8-Dichloromethylene dihydroberberine (200 mg, 0.478 mmol) was weighed and placed into the reaction bottle, and 5 ml 95% ethanol was added in the reaction bottle and the mixture was well-mixed. Then, methanesulfonic acid (93 μl, 1.434 mmol) was added in batchwise and, after finishing, the reaction mixture was reacted for 1 h under stirring and refluxing on 80° C. oil bath under heating. The reaction mixture was cooled to room temperature. 10 ml diethyl ether anhydrous was added in the reaction mixture to make the product precipitated. Filtration was conducted under reduced pressure. The filter cake was washed using diethyl ether anhydrous and tetrahydrofuran until the filtrate was colourless. The filter cake was dried under vacuum to yield 8-dichloromethyl-berberine methanesulfonate red solid 213 mg in yield 86.6%. NMR (500 MHz, DMSO-d$_6$) δ: 9.21 (s, 1H, ArCH=C), 9.20 (s, 1H, CHCl$_2$), 8.33 (d, J =9.0 Hz, 1H, ArH), 8.15 (d, J=9.0 Hz, 1H, ArH), 7.85 (s, 1H, ArH), 7.16 (s, 1H, ArH), 6.21 (s, 2H, OCH$_2$O), 5.26 (br t-like, 2H, NCH$_2$CH$_2$), 4.12 (s, 3H, ArOCH$_3$), 4.06 (s, 3H, ArOCH$_3$), 3.30 (br t-like, 2H, NCH$_2$CH$_2$), 2.31 (s, 3H, CH$_3$SO$_3$); $^{13}$C NMR (100 MHz, DMSO-d$_6$) δ: 153.37, 150.33, 147.66, 147.02, 142.61, 140.74, 134.86, 131.59, 126.67, 125.35, 124.50, 120.60, 119.84, 107.81, 106.02, 102.17, 62.83, 62.37, 57.24, 52.96, 25.79, 18.45.

Example 21. Preparation Process and Structure Identification Data of Compound 41

8-Dichloromethylene dihydrocoptisine (200 mg, 0.497 mmol) was weighed and placed into the reaction bottle, and 5 ml 95% ethanol was added in the reaction bottle and the mixture was well-mixed. Then, ethanesulfonic acid (122 μl, 1.492 mmol) was added in batchwise and, after finishing, the reaction mixture was reacted for 1 h under stirring and refluxing on 80° C. oil bath under heating. The reaction mixture was cooled to room temperature. Filtration was conducted under reduced pressure. The filter cake was washed using tetrahydrofuran and diethyl ether anhydrous and until the filtrate was colourless. The filter cake was dried under vacuum to yield 8-dichloromethyl-coptisine ethanesulfonate red solid 171 mg in yield 67.1%. $^1$H NMR (400 MHz, DMSO-d$_6$) δ: 9.21 (s, 1H, ArCH=C), 8.68 (s, 1H, CHCl$_2$), 8.16 (d, J=8.8 Hz, 1H, ArH), 7.98 (d, J=8.8 Hz, 1H, ArH), 7.84 (s, 1H, ArH), 7.16 (s, 1H, ArH), 6.57 (s, 2H, OCH$_2$O), 6.21 (s, 2H, OCH$_2$O), 5.22 (t, 2H, J=5.6 Hz, NCH$_2$CH$_2$), 3.29 (t, 2H, J=6.0 Hz, NCH$_2$CH$_2$), 2.35 (q, 2H, J=7.2 Hz, CH$_3$CH$_2$SO$_3^-$), 1.03 (t, J=7.2 Hz, 3H, CH$_3$CH$_2$SO$_3$).

Example 22. Preparation Process and Structure Identification Data of Compound 43

8-Dichloromethylene dihydroberberine (200 mg, 0.478 mmol) was weighed and placed into the reaction bottle, and 5 ml 95% ethanol was added in the reaction bottle and the mixture was well-mixed. Then, ethanesulfonic acid (117 μl, 1.434 mmol) was added in batchwise and, after finishing, the reaction mixture was reacted for 1 h under stirring and refluxing on 80° C. oil bath under heating. The reaction mixture was cooled to room temperature. 10 ml diethyl ether anhydrous was added in the reaction mixture to make the product precipitated. Filtration was conducted under reduced pressure. The filter cake was washed using diethyl ether anhydrous and tetrahydrofuran until the filtrate was colourless. The filter cake was dried under vacuum to yield 8-dichloromethyl-berberine ethanesulfonate red solid 193 mg in yield 76.4%. NMR (400 MHz, DMSO-$d_6$) δ: 9.21 (s, 1H, ArCH=C), 9.19 (s, 1H, CHCl$_2$), 8.33 (d, J=9.2 Hz, 1H, ArH), 8.14 (d, J=9.2 Hz, 1H, ArH), 7.85 (s, 1H, ArH), 7.16 (s, 1H, ArH), 6.21 (s, 2H, OCH$_2$O), 5.26 (t, J=6.0 Hz, 2H, NCH$_2$CH$_2$), 4.12 (s, 3H, ArOCH$_3$), 4.05 (s, 3H, ArOCH$_3$), 3.30 (t, J=6.0 Hz, 2H, NCH$_2$CH$_2$), 2.37 (q, J=7.6 Hz, 2H, CH$_3$CH$_2$SO$_3$), 1.05 (t, J=7.6 Hz, 3H, CH$_3$CH$_2$SO$_3$); $^{13}$C NMR (100 MHz, DMSO-$d_6$) δ: 153.37, 150.34, 147.66, 147.03, 142.62, 140.74, 134.86, 131.59, 126.67, 125.34, 124.50, 120.60, 119.85, 107.81, 106.01, 102.17, 62.83, 62.37, 57.24, 52.96, 45.05, 25.79, 9.79.

Example 23. Preparation Process and Structure Identification Data of Compound 45

8-Dichloromethylene dihydrocoptisine (500 mg, 1.243 mmol) was weighed and placed into the reaction bottle, and 7 ml 95% ethanol was added in the reaction bottle and mixed up. Then, benzenesulfonic acid (588 mg, 3.728 mmol) was added in batchwise and, after finishing, the reaction mixture was reacted for 1.5 h under stirring and refluxing on 80° C. oil bath under heating. The reaction mixture was cooled to room temperature and the product was precipitated. Filtration was conducted under reduced pressure. The filter cake was washed using a small amount of 95% ethanol solution. The filter cake was dried under vacuum to yield bis(8-dichloromethyl-coptisine) monobenzenesulfonate red solid 574 mg in yield 96.0%. $^1$H NMR (500 MHz, DMSO-$d_6$) δ: 9.20 (s, 1H, ArCH=C), 8.68 (s, 1H, CHCl$_2$), 8.17 (d, J=8.7 Hz, 1H, ArH), 7.99 (d, J=8.7 Hz, 1H, ArH), 7.84 (s, 1H, ArH), 7.58 (m, 1H, ArH), 7.30 (m, 1.5 H, ArH), 7.16 (s, 1H, ArH), 6.57 (s, 2H, OCH$_2$O), 6.21 (s, 2H, OCH$_2$O), 5.22 (t, J=6.0 Hz, 2H, NCH$_2$CH$_2$), 3.29 (t, J=6.0 Hz, 2H, NCH$_2$CH$_2$).

Example 24. Preparation Process and Structure Identification Data of Compound 47

8-Dichloromethylene dihydroberberine (500 mg, 1.195 mmol) was weighed and placed into the reaction bottle, and 3.5 ml 95% ethanol was added in the reaction bottle and the mixture was well-mixed. Then, benzenesulfonic acid (567 mg, 3.585 mmol) was added in batchwise and, after finishing, the reaction mixture was reacted for 1.5 h under stirring and refluxing on 80° C. oil bath under heating. The reaction mixture was cooled to 0° C. gradually to precipitate the crystal. Filtration was conducted under reduced pressure. The filter cake was washed using a small amount of 95% ethanol solution. The filter cake was dried under vacuum to yield 8-dichloromethyl-berberine benzenesulfonate red solid 366 mg in yield 53.1%. $^1$H NMR (500 MHz, DMSO-$d_6$) δ: 9.21 (s, 1H, ArCH=C), 9.19 (s, 1H, CHCl$_2$), 8.32 (d, J =9.2 Hz, 1H, ArH), 8.15 (d, J=9.2 Hz, 1H, ArH), 7.86 (s, 1H, ArH), 7.59 (m, 2H, ArH), 7.31 (m, 3H, ArH), 7.16 (s, 1H, ArH), 6.21 (s, 2H, OCH$_2$O), 5.26 (t, J=6.0 Hz, 2H, NCH$_2$CH$_2$), 4.12 (s, 3H, ArOCH$_3$), 4.05 (s, 3H, ArOCH$_3$), 3.30 (t, J=6.0 Hz, 2H, NCH$_2$CH$_2$).

Example 25. Preparation Process and Structure Identification Data of Compound 49

8-Dichloromethylene dihydrocoptisine (200 mg, 0.497 mmol) was weighed and placed into the reaction bottle, and 5 ml 95% ethanol was added in the reaction bottle and the mixture was well-mixed. Then, naphthalenesulfonic acid (311 mg, 1.492 mmol) was added in batchwise and, after finishing, the reaction mixture was reacted for 1 h under stirring and refluxing on 80° C. oil bath under heating. The reaction mixture was cooled to room temperature and the product was precipitated. Filtration was conducted under reduced pressure. The filter cake was washed using tetrahydrofuran until the filtrate was colourless. The filter cake was dried under vacuum to yield 8-dichloromethyl-coptisine 2-naphthalenesulphonate red crystalline 250 mg in yield 82.4%. $^1$H NMR (400 MHz, DMSO-$d_6$) δ: 9.20 (s, 1H, ArCH=C), 8.67 (s, 1H, CHCl$_2$), 8.17 (d, J=8.8 Hz, 1H, ArH), 8.13 (br s, 1H, ArH), 7.98 (d, J=8.8 Hz, 1H, ArH), 7.97 (ov, 1H, ArH), 7.89 (m, 1H, ArH), 7.85 (d, J=8.8 Hz, 1H, ArH), 7.84 (s, 1H, ArH), 7.70 (dd, J=8.4, 1.2 Hz, 1H, ArH), 7.52 (m, 2H, ArH), 7.16 (s, 1H, ArH), 6.57 (s, 2H, OCH$_2$O), 6.21 (s, 2H, OCH$_2$O), 5.22 (t, 2H, J=5.6 Hz, NCH$_2$CH$_2$), 3.29 (t, 2H, J=6.0 Hz, NCH$_2$CH$_2$).

Example 26. Preparation Process and Structure Identification Data of Compound 51

8-Dichloromethylene dihydroberberine (200 mg, 0.478 mmol) was weighed and placed into the reaction bottle, and 5 ml 95% ethanol was added in the reaction bottle and the mixture was well-mixed. Then, 2-naphthalenesulfonic acid (299 mg, 1.434 mmol) was added in batchwise and, after finishing, the reaction mixture was reacted for 1 h under stirring and refluxing on 80° C. oil bath under heating. The reaction mixture was cooled to room temperature. 10 ml diethyl ether anhydrous was added in the reaction mixture to make the product precipitated. Filtration was conducted under reduced pressure. The filter cake was washed using diethyl ether anhydrous. The filter cake was dried under vacuum to yield 8-dichloromethyl-berberine 2-naphthalenesulphonate red solid 62 mg in yield 20.7%. $^1$H NMR (400 MHz, DMSO-$d_6$) δ: 9.21 (s, 1H, ArCH=C), 9.19 (s, 1H, CHCl$_2$), 8.32 (d, J=9.2 Hz, 1H, ArH), 8.14 (d, J=9.2 Hz, 1H, ArH), 8.13 (s, 1H, ArH), 7.96 (m, 1H, ArH), 7.89 (m, 1H, ArH), 7.85 (m, 2H, ArH), 7.70 (dd, J=8.4, 1.6 Hz, 1H, ArH), 7.52 (m, 2H, ArH), 7.16 (s, 1H, ArH), 6.21 (s, 2H, OCH$_2$O), 5.26 (t, J=6.0 Hz, 2H, NCH$_2$CH$_2$), 4.12 (s, 3H, ArOCH$_3$), 4.05 (s, 3H, ArOCH$_3$), 3.30 (t, J=6.0 Hz, 2H, NCH$_2$CH$_2$); NMR (100 MHz, DMSO-$d_6$) δ: 153.36, 150.34, 147.66, 147.02, 145.57, 142.60, 140.74, 134.85, 132.56, 132.02, 131.57, 128.31, 127.31, 127.14, 126.65, 126.26, 126.14, 125.33, 124.49, 123.88 (2×C), 120.59, 119.83, 107.81, 106.00, 102.17, 62.82, 62.36, 57.22, 52.96, 25.79.

2. Test Examples of Solubility Examination on the Compounds of the Invention

Example 1. Test Example of Hydrosolubility Examination on the Compounds of the Invention The compounds of the invention were weighed and placed into a certain amount of pure water solvent under 25° C.±2°

C., respectively. The water solution containing the compounds of the invention was shaken forcefully every 5 minutes for 30 seconds and the dissolution status within 30 minutes was observed. If there were no visible solute particle, it would be regarded as complete dissolution.

Experimental results: The solubility was determined at 25° C.±2° C. of temperature and the amount of the compounds of the invention dissolved in one milliliter of purified water are 8-dichloromethyl coptisine hydrochloride (1) 5 mg, 8-dichloromethyl berberine hydrochloride (3) 35 mg, 8-dichloromethyl coptisine hydrogen oxalate (21) 5.25 mg, 8-dichloromethyl berberine hydrogen oxalate (23) 5.1 mg, 8-dichloromethyl coptisine hydrogen maleate (25) 3.71 mg, 8-dichloromethyl berberine hydrogen maleate (27) 3.83 mg, 8-dichloromethyl coptisine tosylate (29) 1.5 mg, 8-dichloromethyl berberine tosylate (31) 5.0 mg, 8-dichloromethyl coptisine benzenesulfonate (45) 8.9 mg, and 8-dichloromethyl berberine benzenesulfonate (47) 6.45 mg, respectively. In parallel determination, the amount of quaternary coptisine chloride and quaternary berberine chloride as quaternary ammonium salt substrates of berberine-type alkaloids that can be dissolved in each milliliter of water is less than 1 mg and 2 mg, respectively.

Example 2. Test Example of Alcohol-Solubility Examination on the Compounds of the Invention The compounds of the invention were weighed and placed into different amount of 95% ethanol solvent under refluxing, respectively. The dissolution status within 30 minutes was observed. If there were no visible solute particle, it would be regarded as complete dissolution.

Experimental results: When examining under refluxing condition, the amount of 95% ethanol solvent required for dissolving each gram of the compounds of the invention are 8-dichloromethyl coptisine hydrochloride (1) 23 ml, 8-dichloromethyl coptisine hydrogen maleate (25) 23 ml, 8-dichloromethyl berberine hydrogen maleate (27) 5.8 ml, 8-dichloromethyl coptisine tosylate (29) 24 ml, 8-dichloromethyl berberine tosylate (31) 7 ml, and 8-dichloromethyl berberine benzenesulfonate (47) 7 ml, respectively.

3. Experimental Examples of the Pharmacological Efficacy and Toxicology Evaluation on the Compounds of the Invention Example 1: Evaluation on the Anti-Microbial Activity of the Compounds of the Invention 1. Materials and Methods
(1) Strains: *Staphylococcus aureus, Escherichia colt, Candida albicans* MCC (F) 98001.
(2) Experimental method: the anti-bacterial activity of the compounds of the invention was evaluated by determining the minimum inhibitory concentration (MIC) using the twofold microdilution broth method. The compounds of the invention and the reference substances (quaternary ammonium salt substrates of berberine-type alkaloids and levofloxacin) were prepared into a 20000 µg/ml stock solution with DMSO for use. *S. aureus* and *E. coli* were diluted using MHB (Mueller Hinton Broth) medium, and *C. albicans* using Sabouraud medium, all prepared into $10^6$ CFU (colony forming unit) concentration as bacterial suspensions for use. The determination steps of MIC are as follows. First, 180 µl of MHB medium (for *S. aureus* and *E. coli*) or Sabouraud Medium (for *C. albicans*) was transferred to the first well in each row of the sterile 96 well plate, and 100 µl to the second to the 11th wells of each row, and 200 µl to the 12th well as negative blank control well. 20 µl sample stock solution was taken and added to the first well. After mixed up, 100 µl was taken from the first well and transferred to the second well. The same as mentioned above, the second well was mixed up, 100 µl of mixed content was taken from the second well and added to the third well, as described above. As such, the same operation was continued till the 10th well, and finally 100 µl of content was drawn from the 10th well and discarded. The bacterial suspension of 100 µl was added to each of the aforementioned from first to eleven wells and mixed up. Three parallel groups for each sample were set up. The 96 well plates were put into the incubator to culture for 24 h. The temperature to determine the MIC of the compounds of the invention against *S. aureus* and E. was set at 37° C. and that of *C. albicans* at 25° C. The MIC values of each sample to be tested as well as those of the references were observed and recorded with the naked eyes.

2. Experimental Results
See table 1

TABLE 1

MIC values determination result of the compounds of the invention in anti-microbial experiment

| Compounds | MIC (ug/mL) | | |
|---|---|---|---|
| | S. aureus | E. coli | C. albicans |
| berberine hydrochloride | 125 | 250 | 250 |
| coptisine hydrochloride | >250 | >250 | 250 |
| 1 | 15.6 | 62.5 | <1.95 (0.78)$^a$ |
| 3 | 31.2 | >250 | 3.9 |
| Levofloxacin | <1.95 | <1.95 | >250 |

Note:
"—" indicates no determination being conducted; "a" indicates that when the concentration of the stock solution of compounds to be tested was reduced to 2000 µg/ml to further determine the MIC value, the test result was 0.78 µg/ml.

Although the action intensity of the compounds of the invention against *S. aureus* and *E. coli* is lower than that of positive control levofloxacin in MIC evaluation, because the compounds of the invention are nontoxic and hypotoxic bioactive compounds, they have a broader application prospect even than levofloxacin. And the intensity of pharmacological action of the compounds of the invention against *C. albicans* is significantly higher in MIC evaluation than that of the positive control levofloxacin (the MIC of levofloxacin is more than 250 µg/ml).

Example 2: Anti-Inflammatory Pharmacodynamics Evaluation of the Compounds of the Invention with the Acute Ear Swelling Model of Mice Caused by Croton Oil 1. Materials and Methods
(1) Animals: Balb/c mice, male (20-22 g); eight mice in each group.
(2): Grouping: The experiment was divided into model group, positive drug indomethacin (Sigma company) group, the invention compound 1 administration group, and the invention compound 3 administration group.
(3) Dosage and times of administration: 5 mg/kg for positive drug; on test of compounds 1 and 3 of the invention, the dosage was both 100 mg/kg, once a day for three days.
(4) Experimental methods: the mice in the model group were administrated 0.9% normal saline (dosage volume: 10 ml/kg) by the intragastrical administration. In the positive drug group, the positive drug was prepared by 5 mg/kg of dosage using 0.9% normal saline as the solvent and was administrated by gavage (dosage volume: 10 ml/kg). In the compounds of the invention administration groups, the compounds were prepared by 100 mg/kg of dosage using 0.9% normal saline as the solvent and were administrated by gavage (dosage volume: 10 ml/kg). After the last administration, all mice were induced to inflammation by daubing 20 μl of croton oil acetone solution on both sides of the right ear, the left ear not daubed as normal control ear. After 4 hours of modeling, the mice were killed, the ears were cut off along the auricle baseline, and the ear pieces of each subject were taken off at the counterpart place of each ear with a perforator and weighed. The difference between the weight of the right ear piece and that of the left ear piece indicated the degree of inflammatory swelling. The inhibition rate of drugs on ear swelling (%) was calculated by comparing the ear swelling degree values of each administration group and positive drug group with the data of model group.

Inhibition rate (%)=[(swelling degree of model group–swelling degree of administration group)/ swelling degree of model group]×100 (%)

(5) Statistical analysis: The experimental results were expressed as 'mean±sd'. The statistical differences between the two groups were calculated and analyzed by t-test method. #, indicates P<0.05 (compared with the model group); and ##, P<0.01 (compared with the model group).

2. Experimental Results
See Table 2.

TABLE 2

The swelling inhibition test results of compounds 1 and 3 of the invention in the acute swelling model of mouse ear caused by croton oil

| Groups | Number of cases (pieces: start/end) | Degree of swelling (mg) | Inhibition rate (%) |
|---|---|---|---|
| Model(croton oil) | 8/8 | 94.95 ± 18.42 | 0 |
| Indomethacin (5 mg/kg) | 8/8 | 70.26 ± 20.97# | 26.01# |
| 1 (100 mg/kg) | 8/8 | 41.24 ± 16.01## | 56.59## |
| 3 (100 mg/kg) | 8/8 | 85.19 ± 39.24 | 10.33 |

Note:
P <0.05, ##P <0.01, compared with the model group.

3. Results Analysis (1) Compared with the model group, indomethacin, a positive drug, had a strong inhibition effect on ear swelling (#P<0.05), suggesting that the experimental system was reasonable, accurate, and reliable.

(2) Compared with the model group, compound 1 group showed significant anti-inflammatory activity, statistically significant difference being obtained, ##P<0.01. Compared with the model group, compound 3 showed anti-inflammatory activity, but the anti-inflammatory activity was weaker than compound 1 and positive control.

4. Conclusion: In the case of 100 mg/kg dosage for intragastric administration, compound 1 has strong anti-swelling activity for mouse ear caused by croton oil, while compound 3 has anti-inflammatory activity, but it is relatively weak.

Although the administration dosage of the compounds of the invention in the experiment was greater than 5 mg/kg of the positive control drug indomethacin, also in view of the fact that the compounds of the invention have the prominent features of being nontoxic or hypotoxic bioactive compounds, and the compounds of the invention are not homologous compound of indomethacin, and, considering the effectiveness and safety of drugs comprehensively (drug research cannot only consider the intensity of pharmacological action, the safety of drugs is even more important), the fact that in the case of large dosage of the compounds of the invention, the anti-inflammatory effect was stronger than that of the positive control drug and the experimental animal can endure high doses of the compounds of the invention just demonstrate that the compounds of the invention have more application value than the positive control drug in the preparation of drugs for preventing, alleviating and/or treating inflammation.

Example 3: Biological Research and Implementation Example of the Compounds of the Invention Against Ulcerative Colitis 1. Materials and Methods (1) Animals: C57b1/6j mice, male (20-22 g); seven mice in each group.

(2) Grouping: The experiment was divided into normal control group, dextran sodium sulfate (DSS) model group, the first positive drug (SASP) group, the second positive drug (dihydroberberine) group, and the invention compound 1 and 3 administration groups.

(3) Dosage and times of administration: The positive drug was 500 mg/kg, both dihydrocoptisine and the compounds of the invention were 100 mg/kg, once a day for eight days.

(4) Experimental methods: The method of this experiment was a literature method: see Zhi-Hui Zhang, Hai-Jing Zhang, An-Jun Deng, Bo Wang, Zhi-Hong Li, Yang Liu, Lian-Qiu Wu, Wen-Jie Wang, and Hai-Lin Qin. Synthesis and Structure-activity Relationships of Quaternary Coptisine Derivatives as Potential Anti-ulcerative Colitis Agents. Journal of Medicinal Chemistry. 2015, 58, 7557-7571.

2. Results and discussion: The compounds of the invention had significant therapeutic effect on acute C57b1/6j mice ulcerative colitis induced by dextran sodium sulfate (DSS) in vivo.

(1) The compounds of the invention could effectively reduce the body weight loss of C57b1/6j mice model of ulcerative colitis induced by DSS (see Table 3).

It can be seen from Table 3 that, after the ending of the experiment, compared with the initial value of body weight of animals in each group, the body weight of animals in the normal control group increased by 0.09%. In the model group, the body weight of animals decreased by 27.61% (**, P<0.01, compared with the normal control group). The body weight of animals in positive drug SASP group decreased by 27.70% at the administration dosage of 500 mg/kg, and the body weight of the animals in the positive drug dihydrocoptisine administration group decreased by 18.77%# (#P<0.05, compared with the model group) at the administration dose of 100 mg/kg. While, the body weight of the animals in the compounds of the invention 1 and 3 administration groups decreased by 8.19%## (##P<0.01, compared with the model group) and 25.54%, respectively, at the administration dose of 100 mg/kg. Therefore, the compounds of the invention can slow down or significantly slow down the body weight loss of model animals, statistically significant difference from the model group being shown. The experimental results showed that, at the dose of 100 mg/kg, the compounds of the invention can effectively alleviate the body weight loss of C57b1/6j mice with experimental ulcerative colitis to a certain extent. In addition, compound 1 is apparently superior to dihydrocoptisine in improving the body weight loss of ulcerative colitis model animals (in fact, there is a huge difference between the two structures), and compound 3 is also superior to the positive drugs.

TABLE 3

Influence of the compounds of the invention on the body weight of C57b1/6j mice with ulcerative colitis

| Groups | Number of cases (pieces: start/end) | Body weight (g) X ± SD Start | Body weight (g) X ± SD End | Body weight change rate (%) |
|---|---|---|---|---|
| Normal control group | 7/7 | 22.84 ± 0.42 | 22.86 ± 0.90 | +0.09 |
| Model group (DSS induction) | 7/7 | 22.94 ± 1.32 | 16.65 ± 1.95 | −27.61** |
| SASP group (500 mg/kg)[a] | 7/7 | 22.10 ± 1.42 | 15.86 ± 1.58 | −27.70 |
| Dihydrocoptisine (100 mg/kg)[a] | 7/7 | 22.69 ± 0.77 | 18.43 ± 2.01 | −18.77[#] |
| 1 (100 mg/kg) | 7/7 | 21.34 ± 0.50 | 19.60 ± 0.93 | −8.19[##] |
| 3 (100 mg/kg) | 7/7 | 21.86 ± 0.59 | 16.28 ± 0.69 | −25.54 |

Notes:
[a]Positive control group; **P <0.01, compared with the normal control group; [#]P <0.05 and [##]P <0.01, compared with model group.

(2) The improving effect of the compounds of the invention on the colon contracture of C57b1/6j mice model of ulcerative colitis induced by DSS (see Table 4).

Table 4 shows the colon length of each group and the percentage of colon contracture compared with the normal control group in the end of the experiment. The results showed that, compared with the normal control group which had the colon length of 8.19 cm, the colon length of the model group mice was significantly shorter, which was 5.21 cm (**, P<0.01, compared with the normal control group). At the administration dose of 100 mg/kg used in the experiment, compared with the model group mice, the colon length of the mice in each administration group of the compounds of the invention was significantly longer. The colon length of mice of compound 1 group was 6.85 cm[##] ([##], P<0.01, compared with the model group), and compound 3 was 5.83 cm ([#], P<0.05, compared with the model group). The colon length of mice in positive drug SASP group was 5.90 cm[#] ([#], P<0.05, compared with the model group) at the administration dose of 500 mg/kg. The colon length of mice in positive drug dihydrocoptisine administration group was 6.23 cm ([##], P<0.01, compared with the model group) at the administration dose of 100 mg/kg. Compared with the normal control group, compound 1 of the invention showed obvious improvement effect on the colon contracture of C57b1/6j mice model of ulcerative colitis induced by DSS, superior to the positive drug and the active compound dihydrocoptisine. Compound 3 also showed obvious activity.

(3) The effect of the compounds of the invention on disease activity index (DAI) and DAI inhibition rate of C57b1/6j mice model of ulcerative colitis induced by DSS (Table 5).

DAI score was used to evaluate therapeutic effect of active compounds via body weight loss percentage of animals, fecal characteristics, and fecal blood, and the like, which are closely related to clinical symptoms of ulcerative colitis. The lower DAI score and the higher DAI inhibition rate indicated that the model animal was more close to the normal physiological status after treatment. The effect of the compounds of the invention on the disease activity index (DAI) and the inhibition rate of DAI in the C57b1/6j mice model of ulcerative colitis induced by DSS was investigated. The results showed that the compounds of the invention have significant anti-ulcerative colitis activity. At the administration dose of 100 mg/kg used in the experiment, the anti-ulcerative colitis activity of the compounds of the invention were significantly higher than that of positive drug SASP at the administration dose of 500 mg/kg, and also higher than that of positive drug dihydrocoptisine at the administration dose of 100 mg/kg. In Table 5, **, P<0.01, compared with the normal control group; [#], P<0.05 and [##], P<0.01, compared with the model group.

TABLE 5

The effect of the compounds of the invention on disease activity index (DAI) and DAI inhibition rate of C57b1/6j mice model of acute ulcerative colitis induced by DSS

| Groups | Number of cases (pieces: start/end) | DAI | DAI inhibition rate (%) |
|---|---|---|---|
| Normal control group | 7/7 | 0.17 ± 0.18 | – |
| Model group (DSS induction) | 7/7 | 4.00 ± 0.00** | 0 |

TABLE 4

The effect of the compounds of the invention on the colon contracture in C57b1/6j mice ulcerative colitis model animals induced by DSS

| Groups | Number of cases (pieces: start/end) | Colon length (cm) | Percentage of colon contracture (%) |
|---|---|---|---|
| Normal control group | 7/7 | 8.19 ± 0.39 | 0 |
| Model group (DSS induction) | 7/7 | 5.21 ± 0.48** | 36.34** |
| SASP group (500 mg/kg)[a] | 7/7 | 5.90 ± 0.30[#] | 28.43[#] |
| Dihydrocoptisine (100 mg/kg)[a] | 7/7 | 6.23 ± 0.14[##] | 23.93[##] |
| 1 (100 mg/kg) | 7/7 | 6.85 ± 0.56[##] | 16.37[##] |
| 3 (100 mg/kg) | 7/7 | 5.83 ± 0.27[#] | 28.83[#] |

Notes:
[a]Positive control group; **P <0.01, compared with the normal control group; [#]P <0.05 and [##]P <0.01, compared with model group.

TABLE 5-continued

The effect of the compounds of the invention on disease activity index (DAI) and DAI inhibition rate of C57bl/6j mice model of acute ulcerative colitis induced by DSS

| Groups | Number of cases (pieces: start/end) | DAI | DAI inhibition rate (%) |
|---|---|---|---|
| SASP group (500 mg/kg)[a] | 7/7 | 3.07 ± 1.01[#] | 23.33[#] |
| Dihydrocoptisine (100 mg/kg)[a] | 7/7 | 2.24 ± 0.97[##] | 44.03[##] |
| 1 (100 mg/kg) | 7/7 | 1.39 ± 0.61[##] | 65.17[##] |
| 3 (100 mg/kg) | 7/7 | 1.96 ± 0.87[##] | 51.00[##] |

Notes:
[a]Positive control group; **P <0.01, compared with the normal control group; #P <0.05 and ##P <0.01, compared with model group.

Example 4: The Regulation Experiment and Results of Compounds 1 and 3 of the Invention on Tumorigenesis-Related Target Molecules in Six Different Tumor Cells 1. Materials and Methods (1) Cells: Rat glioma cell C6, human large cell lung cancer cell NCIH460, human breast cancer cell MDA-MB-231, human colon cancer cell HCT116, human liver cancer cell 7721, and human osteosarcoma cell MG63.

(2) Experimental method: Rat glioma cell C6, human large cell lung cancer cell NCIH460, human breast cancer cell MDA-MB-231, human colon cancer cell HCT116, human liver cancer cell 7721, and human osteosarcoma cell MG63 were cultured in vitro conventionally. When the above six cells grew to 80% confluent state, they were divided into six well plates. Pre-protection was carried out for three hours with the compounds 1 and 3 of the invention with a concentration of 1 μM. After that, LPS was added to stimulate for 24 hours, and the samples were collected and frozen.

The prepared cell samples were broken by ultrasound in RIPA lysate. After 4-degree cracking for 30 min and centrifuging at 13000 rpm for 10 min, the supernatant was taken. The protein concentration was determined by Brandford method. According to the protein concentration, the same amount of protein was taken and detected by Western blot (WB).

The operation of WB experimental detection is as follows: 4% concentrated glue and 8% separating glue were prepared according to standard SDS-PAGE method. The cytolysis supernatant containing the same concentration of protein was mixed with 5×SDS sample-adding buffer, which was boiled for 5 min and sample-added after cooling. After electrophoresis, it was transferred to PVDF membrane using wet transfer. TBST (0.1% Tween-20; 10 mmol/L Tris-Cl, pH7.5; 3% BSA; 150 mmol/L NaCl) was used to block the non-specific binding site at 4° C. overnight. Membrane washing was done with TBST solution, 10 min/time×3 times. The membrane was incubated with diluted primary antibody (1:500) at room temperature for 3 h. Membrane washing was done with TBST solution, 10 min/time×3 times. The membrane was transferred into the second antibody (1:1000 dilution) and reacted at room temperature for 2 h. Membrane washing was done with TBST solution, 10 min/time×3 times. The membrane was made flat, the luminescent liquid was added dropwise, and imaging was done with chemiluminescence. The results showed that compounds 1 and 3 of the invention have regulatory effects on the signal molecules of STAT3, NF-κB, E-Cadherin, and PCNA closely related to the pathogenesis of glioma, lung cancer, colon cancer, liver cancer, breast cancer, and osteosarcoma at the protein level, exhibiting obvious anticancer activity, as shown in FIG. 1 (A-F).

2. Experimental Results

Under this experimental system, $1\times10^{-8}$ mol/L (i. e. 10 nM) of the series compounds of the invention either had significant inhibitory effects on STAT3, NF-κB, and PCNA, which are signal target molecules closely related to tumorigenesis in tumor cells of colorectal cancer, liver cancer, lung cancer, breast cancer, osteosarcoma, and glioma cells, or promoted the expression of E-cadherin to a certain extent. Thus, they have anticancer activity in the prevention, alleviation and/or treatment of diseases related to colorectal cancer, liver cancer, lung cancer, breast cancer, osteosarcoma, and brain tumor.

3. Conclusions

The series compounds of the invention have significant regulatory effect on signal molecules related to tumorigenesis, shown as either having inhibitory effect to a certain extent on target molecules of STAT3, NF-κB, and PCNA related to tumorigenesis, or having promoting effect on the expression of E-cadherin protein.

FIGS. 1A-F show the effects of compounds 1 and 3 of the invention on the expression of target molecules STAT3, NF-κB, PCNA, and E-cadherin proteins related to tumorigenesis in glioma cell C6, human colon cancer cell HCT116, human large cell lung cancer cell line NCIH460, human liver cancer cell 7721, human osteosarcoma cell MG63, and human breast cancer cell MDA-MB-231.

FIG. 1-A shows the experimental results of compounds 1 and 3 in glioma cell C6. Compared to model group, compounds 1 and 3 significantly promoted the expression of E-cadherin protein, inhibited the expression of NF-κB. Compound 3 could inhibit the expression of PCNA. However, the inhibitory activity of compounds 1 and 3 on pSTAT3 was not detected in C6 cells.

FIG. 1-B shows the experimental results of compounds 1 and 3 in human colon cancer cell HCT116. Compared to model group, compounds 1 and 3 had significant inhibitory effect on pSTAT3. Compounds 1 and 3 also had significant inhibitory activity on NF-κB. However, compounds 1 and 3 had less significant effect on the expression of E-cadherin and PCNA.

FIG. 1-C shows the experimental results of compounds 1 and 3 in human large cell lung cancer cell line NCIH460. Compared to model group, compound 1 could significantly promote the expression of E-cadherin. Compounds 1 and 3 significantly inhibited the expression of pSTAT3. Compounds 1 and 3 also obviously inhibited the expression of NF-κB. However, compounds 1 and 3 had less significant effect on PCNA expression.

FIG. 1-D shows the experimental results of compounds 1 and 3 in human hepatoma cell 7721. Compared to model group, compounds 1 and 3 had very significant inhibitory effect on the expression of NF-κB. However, compounds 1 and 3 had less significant effect on the expression of E-cadherin.

FIG. 1-E shows the experimental results of compounds 1 and 3 in human osteosarcoma cell MG63. Compared to model group, compounds 1 and 3 both significantly inhibited the expression of pSTAT3 and NF-κB.

FIG. 1-F shows the experimental results of compounds 1 and 3 in human breast cancer cell MDA-MB-231. Compared to model group, compounds 1 and 3 significantly inhibited the expression of pSTAT3, and compounds 1 and 3 obviously inhibited the expression of NF-κB. However, compounds 1 and 3 showed less significant effect on PCNA and E-cadherin.

Example 5: Toxicity Test Results of Compounds 1 and 3 of the Invention on 293T Normal Cell Line Cells Cultured in Vitro (1) Experimental method:: 293T normal cell line cells cultured in vitro grown to 90% confluent state were digested with 0.1% trypsin/0.1% EDTA and inoculated into 96 well cell culture plate, $3\times10^3$ cells per well. On the next day of culture, the original culture medium was removed, $1\times10^{-5}$ mol/L (i.e. 10 μM) of working solution of the compounds of the invention were added into each well to continue culture. The same volume of complete cell culture medium was added into the blank control well. The cytotoxicity of the compounds of the invention on the 293T cell was detected by CCK8 method after the 293T cell was co-cultured with the compounds of the invention for 48 hours (n=6). The toxic effect of the compounds of the invention on 293T normal cell line cells was calculated according to the following formula, and expressed in inhibition rate:

Inhibition rate (%)=[(control well absorbance−drug well absorbance)/control well absorbance]×100 (%)

(2) Results: Within the time range of experiment to test, $1\times10^{-5}$ mol/L (i.e. 10 μM) of the series compounds of the invention had no obvious cytotoxicity on 293T normal cell line cells, the inhibition rate was—3.18%-8.54, and there was no significant difference statistically. See Table 6 for cell growth inhibition rate.

TABLE 6

Toxicity test results (inhibition rate) of the compounds of the invention on 293T cells

| The compounds of the invention | Sample concentration (μM) | inhibition rate (%) |
|---|---|---|
| 1 | 10 | 8.54 |
| 3 | 10 | -3.18 |

(3) Conclusion: The series compounds of the invention have no obvious toxicity on the growth of 293T normal cell line cells, and are suitable for downstream activity screening experiment.

Example 6: Acute Toxicity Test Results of the Compounds of the Invention

Kunming mice (18-22 g) were divided into groups, ten mice in each group, half male and half female. Eight dose groups were set up. According to bliss method, the dose of each administration dose group was set up by the design from the highest dose of 5 g/kg in equal order of 1:0.8. Mice were administrated by gavage. The night before the drug administration, animals were not allowed to eat any food but were allowed to drink water. The mice were given normal diet four hours after administration. After a single administration, the indices of mental state, body weight, diet, behavior, secretion, excreta, death, and toxic reaction, and the like, of the animals were observed for 14 consecutive days, and $LD_{50}$ value was calculated. The acute toxicity test results of compounds 1 and 3 of the invention indicated that their LD50 values are as follows: Compound 1 was more than 5.0 g/kg (i.e. LD50 value was not detected), and compound 3 was 600 mg/kg. Compound 1 is a nontoxic specific antibacterial, anti-inflammatory, anti-ulcerative colitis, and anti-tumor compound. Compound 3 is a kind of special antibacterial, anti-inflammatory, anti-ulcerative colitis, and anti-tumor compound with hypotoxicity.

Example 7: The Inhibitory Effect of Compound 1 of the Invention on Tumorigenesis and Growth of Colorectal Cancer Model Mice Induced by (Azoxymethane, AOM)/DSS 1. Experimental Animals
  Male C57b1/6j mice with a body weight range of 18-20 g (purchased from Beijing Huafukang Biotechnology Co., Ltd., License No.: SCXK(Jing)2014-0004).
2. Experimental Groupings
  (1) Normal control group; (2) Model group (AOM/DSS group); (3) Positive drug group (Capecitabine group); (4) Compound 1 group of the invention.
3. Administration Dosage
  (1) Positive drug Capecitabine: 250 mg/kg;
  (2) Compound 1 of the invention: 50 mg/kg.
4. Experimental Method
  C57b1/6j mice were randomly grouped according to the above experimental grouping scheme, five mice in the normal control group, and ten other groups.
  (1) Normal Control Group:
  After one week's normal pre-feeding, normal feeding was done for another two weeks. From the 3rd week on, 0.5% carboxymethylcellulose sodium water solution was administered by gavage in the amount of 10 ml/kg. Administration mode was such that the drug was administered once a day for 12 weeks until the end of the experiment.
  (2) Model Group
  After one week of normal pre-feeding, AOM was given by intraperitoneal injection at a dose of 10 mg/kg (Prepared by a concentration of 10 mg AOM in 10 ml of normal saline). Then the animals were fed normally for one week, which was recorded as the first week of the experiment. At the beginning of the second week, mice were allowed to drink the drinking aqueous solution containing 2% DSS freely for one week. The mice exhibited obvious symptoms of bloody stool and loose stool, etc. From the 3rd week on, 0.5% carboxymethylcellulose sodium water solution was administrated by gavage at the amount of 10 ml/kg. The administration mode was such that the drug was administered once a day for 12 weeks until the end of the experiment. (3) Positive Drug Capecitabine Group
  After one week of normal pre-feeding, AOM was given by intraperitoneal injection at a dose of 10 mg/kg (Prepared by a concentration of 10 mg AOM in 10 ml of normal saline). Then the animals were fed normally for one week, which was recorded as the first week of the experiment. At the beginning of the second week, mice were allowed to drink the drinking water solution containing 2% DSS freely for one week. The mice exhibited obvious symptoms of bloody stool and loose stool, etc. From the 3rd week on, Capecitabine (prepare by a concentration of 250 mg capecitabine in 10 ml of 0.5% sodium carboxymethylcellulose aqueous solution and store at 4° C.) was administered by gavage at a dose of 250 mg/kg (Capecitabine was administered once a day for two consecutive doses. The drug was stopped for one week for each consecutive two week administration), up to the end of the experiment. The administration lasted for 12 weeks (including the weeks of drug withdrawal).

(4) Compound 1 Group of the Invention

After one week of normal pre-feeding, AOM was given by intraperitoneal injection at a dose of 10 mg/kg (prepared by a concentration of 10 mg AOM in 10 ml of normal saline). Then the animals were fed normally for one week, which was recorded as the first week of the experiment. At the beginning of the second week, mice were allowed to drink the drinking water solution containing 2% DSS freely for one week. The mice exhibited obvious symptoms of bloody stool and loose stool, etc. From the 3rd week on, the compound 1 of the invention (prepare by a concentration of 50 mg of compound 1 of the invention in 10 ml of 0.5% sodium carboxymethylcellulose aqueous solution and store at 4° C.) was administered consecutively by gavage at a dose of 50 mg/kg. The administration mode was such that the drug was administered once a day, up to the end of the experiment. The administration lasted for 12 weeks.

At the end of the experiment, the mice were decapitated and killed, changes of spleen weight and colonic tumor burden of the animals after treatment were observed. The experimental results showed that the compounds of the invention exhibited significant antitumor activity in animal in vivo experiment to treat colorectal cancer, and the curative effect was significantly superior to the positive control drug. Specific data is shown in Table 7, FIG. 2, Table 8, and FIG. 3.

5. Experimental Results

FIG. 2 and Table 7 Showed the Effect of Compound 1 of the Invention on Spleen Weight of Colorectal Cancer Model Mice FIG. 2 and Table 7 show that, compared with the spleen weight value (0.088±0.009 g) of normal control group, the spleen weight of the model group increased significantly (0.183±0.026*g), difference in statistics being significant (*, P<0.05, compared with the normal control group). The positive drug capecitabine did not show improvement effect on the spleen weight increase of mice with colorectal cancer at the dose of 250 mg/kg, the spleen weight being 0.228±0.029 g and no significant difference in statistics being observed. While, compound 1 of the invention, at a dose of 50 mg/kg, could significantly reduce the spleen weight of mice with colorectal cancer induced by AOM/DSS, the spleen weight being 0.113±0.013$^\#$ g and difference in statistics being significant ($^\#$, P<0.05, compared with the model group). The results showed that compound 1 of the invention has obvious improvement effect on the spleen weight increase of colorectal cancer mice induced by AOM/DSS.

TABLE 7

Effect of compound 1 of the invention on spleen weight of colorectal cancer model mice

| Groups (Dosage) | Number of cases (mice) start/end | Spleen weight (g) |
|---|---|---|
| Normal control group | 5/5 | 0.088 ± 0.009 |
| Model group (AOM/DSS induction) | 10/10 | 0.183 ± 0.026* |
| Capecitabine (250 mg/kg) | 8/10 | 0.228 ± 0.029 |
| Compound 1 (50 mg/kg) | 8/10 | 0.113 ± 0.013$^\#$ |

Note:
*P <0.05, compared with normal control group; $^\#$P <0.05, compared with model group.

Figure 3:
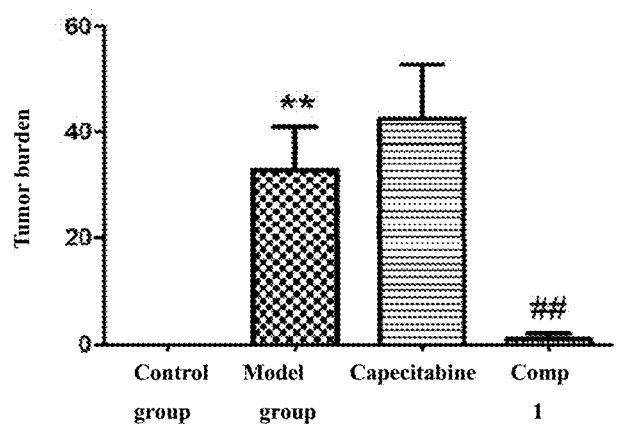

FIG. 3 and Table 8 Show the Effect of Compound 1 of the Invention on the Colorectal Tumor Burden of Colorectal Cancer Model Mice FIG. 3 and Table 8 show that, compared with the relatively calculated value of tumor burden in normal control group (0.00), the tumor burden of mice in colorectal cancer model group increased significantly, the relatively calculated value being 32.76±8.17 and difference in statistics being significant (, P<0.01, compared with the normal control group). The positive drug capecitabine did not show improvement effect on the tumor burden increase of mice with colorectal cancer at the dose of 250 mg/kg, the relatively calculated value of mice being 42.69±10.26 and no significant difference in statistics being observed. While, the compound 1 administration group of the invention has a significant improvement effect on the tumor burden increase of colorectal cancer model mice at a dose of 50 mg/kg, shown as the decrease of tumor number and tumor volume in the whole colon area (including adenoma and adenocarcinoma), the relatively calculated value of tumor burden being 1.13±1.000$^{\#\#}$ and difference in statistics being very significant ($^{\#\#}$, P<0.01) when compared with the colorectal cancer model group. Therefore, the compounds of the invention have significant anti-colorectal cancer effect. Compared with the positive control drug, compound 1 of the invention has very significant curative effect.

The calculation method of calculated tumor burden value is as follows:

Tumor burden=(Mean tumor diameter/numbers of mice)$^2$×(Tumor number/numbers of mice)

TABLE 8

Effect of compound 1 of the invention on colorectal tumor burden of colorectal cancer model mice

| Groups (Dosage) | Number of cases (mice) start/end | Tumor burden (piece) |
|---|---|---|
| Normal control group | 5/5 | 0 |
| Model group (AOM/DSS induction) | 10/10 | 32.76 ± 8.17** |
| Capecitabine (250 mg/kg) | 8/10 | 42.69 ± 10.26 |
| Compound 1 (50 mg/kg) | 8/10 | 1.13 ± 1.00$^{\#\#}$ |

Note:
**P <0.01, compared with normal control group; $^{\#\#}$P <0.01, compared with model group.

What is claimed is:

1. An 8-dihalomethyl berberine-type quaternary ammonium salt compound of quaternized imine-type structure shown as general formula I:

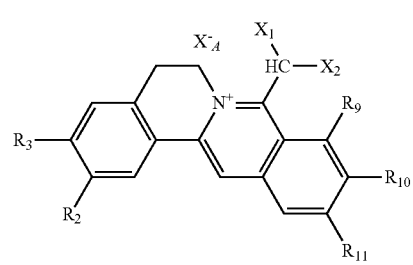

wherein:
R$_2$ and R$_3$ are linked to form alkylene-dioxy;
X$_1$ and X$_2$ are each selected, independently, from F, Cl, Br, or I;
R$_9$ and R$_{10}$ are linked to form alkylene-dioxy and R$_{11}$ is H; and
X$_A$ is monovalent acid radical ion.

2. The 8-dihalomethyl berberine-type quaternary ammonium salt compounds of quaternized imine-type structure according to any one of claim 1, wherein said monovalent acid radical ion X$_A^-$ is selected from the monovalent inorganic or organic acid radical ion.

3. The 8-dihalomethyl berberine-type quaternary ammonium salt compound of quaternized imine-type structure according to claim 2, wherein said monovalent inorganic acid radical ion is selected from halide anions, hydrogen sulfate ion, hydrogen carbonate ion, dihydrogen phosphate ion, hypohalite ion, halite ion, halate ion, perhalate ion, and nitrate ion; said monovalent organic acid radical ion is selected from formate ion, acetate ion, propionate ion, benzoate ion, p-hydroxybenzoate ion, salicylate ion, protocatechuate ion, ferulate ion, isoferulate ion, homogentisate ion, cinnamate ion, p-hydroxycinnamate ion, caffeate ion, phenylacetate ion, tropate ion, gallate ion, veratrate ion, piperonylate, 3,4,5-trimethoxybenzoate ion, orsellinate ion, shikimate ion, (S)-lactate ion, (R)-lactate ion, (±)-lactate ion, (2R,3R)-(+)-hydrogen tartarate ion, (2S,3S)-(−)-hydrogen tartarate ion, (±)-hydrogen tartarate ion, furoate ion, dihydrogen citrate ion, dihydrogen hydroxycitrate ion, hydrogen maleate ion, hydrogen fumarate ion, L-hydrogen malate ion, D-hydrogen malate ion, (dl)-hydrogen malate ion, hydrogen oxalate ion, hydrogen propanedioate ion, hydrogen succinate ion, hydrogen glutarate ion, hydrogen adipate ion, hydrogen pimelate ion, hydrogen suberate ion, hydrogen azelaate ion, hydrogen sebacate ion, benzenesulfonate ion, gluconate ion, ascorbate ion, sulfamate ion, tosylate ion, methanesulfonate ion, ethanesulfonate ion, 2-naphthalene-sulphonate ion, dichloroacetate ion, and difluoroacetate ion.

4. The 8-dihalomethyl berberine-type quaternary ammonium salt compound of quaternized imine-type structure according to claim 2, wherein said monovalent inorganic acid radical ion is selected from halide anions, hydrogen sulfate ion, hydrogen carbonate ion, dihydrogen phosphate ion, hypohalite ion, halite ion, halate ion, perhalate ion, and nitrate ion; said monovalent organic acid radical ion is selected from formate ion, acetate ion, propionate ion, benzoate ion, p-hydroxybenzoate ion, salicylate ion, protocatechuate ion, ferulate ion, isoferulate ion, homogentisate ion, cinnamate ion, p-hydroxycinnamate ion, caffeate ion, phenylacetate ion, tropate ion, gallate ion, veratrate ion, piperonylate, 3,4,5-trimethoxybenzoate ion, orsellinate ion, shikimate ion, (S)-lactate ion , (R)-lactate ion, (±)-lactate ion, (2R,3R)-(+)-hydrogen tartarate ion, (2S,3S)-(−)-hydrogen tartarate ion, (±)-hydrogen tartarate ion, furoate ion, dihydrogen citrate ion, dihydrogen hydroxycitrate ion, hydrogen maleate ion, hydrogen fumarate ion, L-hydrogen malate ion, D-hydrogen malate ion, (dl)-hydrogen malate ion, hydrogen oxalate ion, hydrogen propanedioate ion, hydrogen succinate ion, hydrogen glutarate ion, hydrogen adipate ion, hydrogen pimelate ion, hydrogen suberate ion, hydrogen azelaate ion, hydrogen sebacate ion, benzenesulfonate ion, gluconate ion, and ascorbate ion.

5. The 8-dihalomethyl berberine-type quaternary ammonium salt compound of quaternized imine-type structure according to any one of claim 1, wherein said divalent acid radical ion $XA^{2-}$ is selected from the divalent inorganic or organic acid radical ion.

6. The 8-dihalomethyl berberine-type quaternary ammonium salt compound of quaternized imine-type structure according to claim 5, wherein said divalent inorganic acid radical ion is selected from sulfate ion, carbonate ion, hydrogen phosphate ion; said divalent organic acid radical ion is selected from (2R,3R)-(+)-tartarate ion, (2S,3S)-(−)-tartarate ion, (±)-tartarate ion, hydrogen citrate ion, hydrogen hydroxycitrate ion, maleate ion, fumarate ion, L-malate ion, D-malate ion, (dl)-malate ion, oxalate ion, propanedioate ion, succinate ion, glutarate ion, adipate ion, pimelate ion, suberate ion, azelaate ion, sebacate ion, benzenesulfonate ion with S→O dipolar bond, benzoate ion with two oxygen anion.

7. The 8-dihalomethyl berberine-type quaternary ammonium salt compound of quaternized imine-type structure according to claim 5, wherein said divalent inorganic acid radical ion is selected from sulfate ion, carbonate ion, hydrogen phosphate ion; said divalent organic acid radical ion is selected from (2R,3R)-(+)-tartarate ion, (2S,3S)-(−)-tartarate ion, (±)-tartarate ion, hydrogen citrate ion, hydrogen hydroxycitrate ion, maleate ion, fumarate ion, L-malate ion, D-malate ion, (dl)-malate ion, oxalate ion, propanedioate ion, succinate ion, glutarate ion, adipate ion, pimelate ion, suberate ion, azelaate ion, and sebacate ion.

8. The 8-dihalomethyl berberine-type quaternary ammonium salt compound of quaternized imine-type structure according to any one of claim 1, wherein said alkylenedioxy formed by the attachment of $R_2$ and $R_3$ and $R_9$ and $R_{10}$ is methylenedioxy.

9. The 8-dihalomethyl berberine-type quaternary ammonium salt compound of quaternized imine-type structure according to any one of claim 1, wherein said compound is selected from the group consisting of:

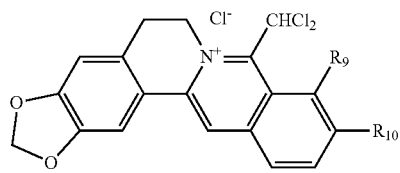

$R_9$ $R_{10}$
1 —OCH$_2$O—
3 OMe OMe

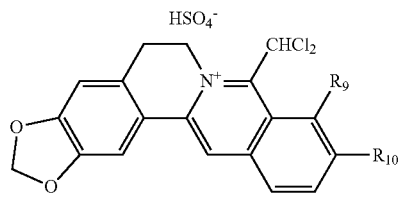

$R_9$ $R_{10}$
5 —OCH$_2$O—
7 OMe OMe

-continued
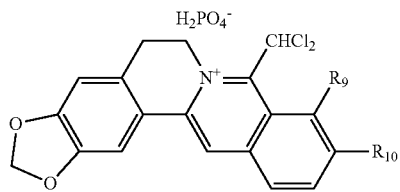
R₉ R₁₀
9 —OCH₂O—
11 OMe OMe
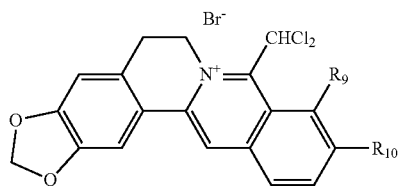
R₉ R₁₀
13 —OCH₂O—
15 OMe OMe
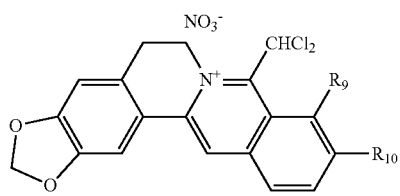
R₉ R₁₀
17 —OCH₂O—
19 OMe OMe
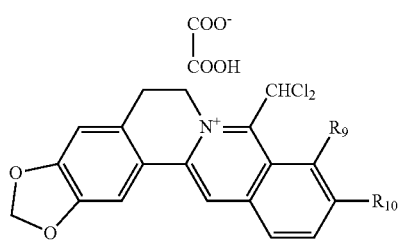
R₉ R₁₀
21 —OCH₂O—
23 OMe OMe
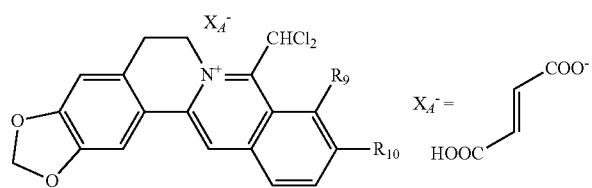
R₉ R₁₀
25 —OCH₂O—
27 OMe OMe -continued
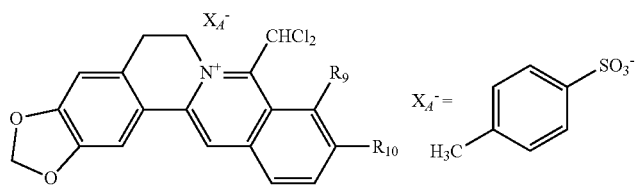
R_9 R_10
29 —OCH_2O—
31 OMe OMe
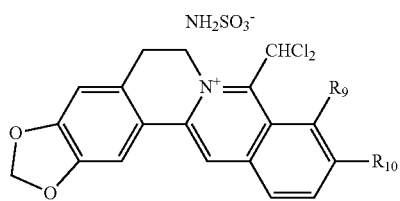
R_9 R_10
33 —OCH_2O—
35 OMe OMe
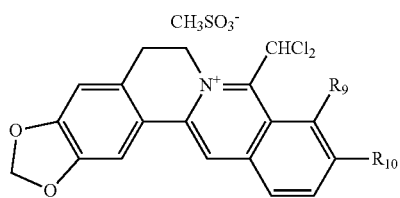
R_9 R_10
37 —OCH_2O—
39 OMe OMe
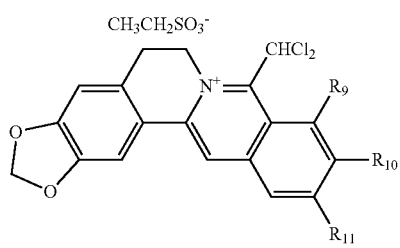
R_9 R_10
41 —OCH_2O—
43 OMe OMe -continued

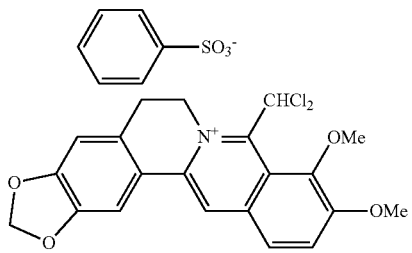

47

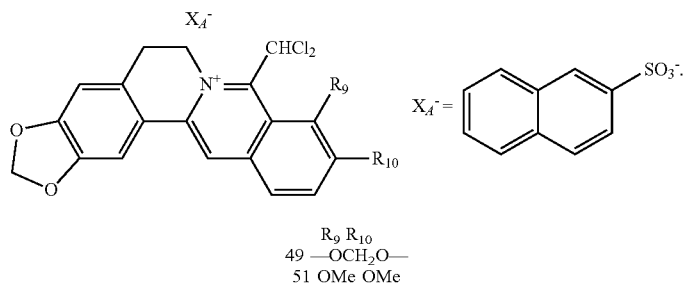

| | R_9 | R_10 |
|---|---|---|
| 49 | —OCH_2O— | |
| 51 | OMe | OMe |

10. The 8-dihalomethyl berberine-type quaternary ammonium salt compounds of quaternized imine-type structure according to any one of claim 1, wherein said compound is selected from the group consisting of:

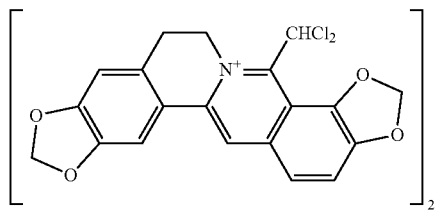

-continued

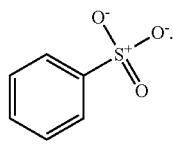

11. A method of treating cancers, microbial infections, inflammations, ulcerative colitis in a patient, comprising administration of the 8-dihalomethyl berberine-type quaternary ammonium salt compound of quaternized imine-type structure according to claim 1 to said patients in need thereof, wherein microorganism comprises gram positive and gram negative bacteria, and the cancer is colorectal cancer, liver cancer, lung cancer, breast cancer, osteosarcoma or glioma and the suitable daily dose range of the compound is 0.1-100 mg/kg by body weight.

* * * * *